(12) United States Patent
Morariu

(10) Patent No.: US 7,776,915 B2
(45) Date of Patent: Aug. 17, 2010

(54) TOPICAL FORMULATIONS AND METHODS OF USE

(75) Inventor: Marius Morariu, Brooklyn, NY (US)

(73) Assignee: Tracie Martyn International, LLC, New York, NY (US)

( * ) Notice: Subject to any disclaimer, the term of this patent is extended or adjusted under 35 U.S.C. 154(b) by 1153 days.

(21) Appl. No.: 11/388,908

(22) Filed: Mar. 24, 2006

(65) Prior Publication Data

US 2006/0216251 A1  Sep. 28, 2006

Related U.S. Application Data

(60) Provisional application No. 60/665,206, filed on Mar. 24, 2005.

(51) Int. Cl.
*A61K 31/20* (2006.01)
*A61K 8/02* (2006.01)
*A61K 36/00* (2006.01)
*A61K 9/127* (2006.01)

(52) U.S. Cl. .................. 514/558; 424/401; 424/450; 424/78.05; 424/70.9; 424/725; 604/20

(58) Field of Classification Search ............. 424/401, 424/450, 78.05, 78.06, 70.9, 775; 604/20; 514/558
See application file for complete search history.

(56) References Cited

U.S. PATENT DOCUMENTS

| | | | |
|---|---|---|---|
| 5,041,643 | A | 8/1991 | Tinti et al. |
| 5,164,394 | A | 11/1992 | Bolund et al. |
| 5,532,409 | A | 7/1996 | Giannessi et al. |
| 5,709,868 | A | 1/1998 | Perricone |
| 5,723,502 | A | 3/1998 | Proctor |
| 5,952,312 | A | 9/1999 | Birkmayer |
| 6,063,108 | A | 5/2000 | Salansky et al. |
| 6,086,789 | A * | 7/2000 | Brunengraber et al. ...... 252/399 |
| 6,224,873 | B1 | 5/2001 | Jones |
| 6,443,915 | B1 * | 9/2002 | Hwang ................ 601/15 |
| 6,455,589 | B1 | 9/2002 | Ames et al. |
| 6,521,669 | B1 * | 2/2003 | Liviero et al. ........... 514/726 |
| 6,528,684 | B1 | 3/2003 | Giannessi et al. |
| 6,752,999 | B2 | 6/2004 | Perricone |
| 6,822,115 | B2 | 11/2004 | Giannessi et al. |
| 6,953,865 | B2 | 10/2005 | Piccoloi |
| 2003/0009158 | A1 | 1/2003 | Perricone |
| 2003/0190337 | A1 | 10/2003 | Bissett |
| 2004/0049247 | A1 | 3/2004 | Perricone |
| 2004/0176448 | A1 * | 9/2004 | Blatt et al. ............ 514/547 |
| 2004/0219114 | A1 | 11/2004 | Andersson et al. |
| 2004/0265345 | A1 | 12/2004 | Perricone |
| 2005/0101669 | A1 * | 5/2005 | Klatt et al. ............ 514/558 |
| 2006/0286046 | A1 * | 12/2006 | Haber ................ 424/59 |

OTHER PUBLICATIONS

Levtchenko, E.N., et al. 2006. Decreased Intracellular AP Content and Intact Mitochondrial Energy Generating Capacity in Human Cystonotic Fibroblasts. *Pediatric Research* 59(2): 287-292.
Ames, Bruce N. 2004. Delaying the Mitochondrial Decay of Aging. *Ann. N. Y. Acad. Sci.* 1019: 406-411.
Ghafoorunissa, S. Hemalatha and M. Vishnu Vardhana Rao. 2004. Sesame lignans enhance attioxidant activity of vitamin E in lipid peroxidation systems. *Molecular and Cellular Biochemistry* 262: 195-202.
Hobart, Laura J., et al. 2004. Anti-crosslinking properties of carnosine: Significance of histidine. *Life Sciences* 75: 1379-1389.
Wu, Xianli, et al. 2004. Development of a database for total antioxidant capacity in foods: a preliminary study. *Journal of Food Composition and Analysis* 17: 407-422.
Greco, Marilena, et al. 2003. Marked aging-related decline in efficiency of oxidative phosphorylation in human skin fibroblasts. *FASEB J.* (online).
Nagasawa, Takashi, et al. 2003. Inhibition of glycation reaction in tissue protein incubations by water soluble rutin derivative, *Molecular and Cellular Biochemistry* 279: 3-10.
Hagen, Tory M., et al. 2002. Feeding acetyl-L-carnitine and lipoic acid to old rats significantly improves metabolic function while decreasing oxidative stress. *Proc. Natl. Acad. Sci. USA* 99(4): 1870-1875.
Liu, Jiankang, et al. 2002. Memory loss in old rats associated with brain mitochondrial decay and RNA/DNA oxidation: Partial reversal by feeding acetyl-L-canitine and/or R-α-lipoic acid. *Proc. Natl. Acad. Sci. USA* 99(4): 2356-2361.
Liu, Jiankang, et al. 2002. Delaying Brain Mitochondrial Decay and Aging with Mitochondrial Antioxidants and Metabolites. *Ann. N.Y. Acad. Sci.* 959: 133-166.
Matsuura, Nobuyasu, et al. 2002. Screening System for the Maillard Reaction Inhibitor from Natural Product Extracts. *Journal of Health Science* 48(6): 520-526.
Musalmah, Mazlan, et al. 2002. Effect of vitamin E on plasma malondialdehyde, antioxidant enzyme levels and the rates of wound closures during wound healing in normal and diabetic rats, *Asia Pacific J. Clin. Nutr.* 11 (Suppl): S448-S451.
Offord, Elizabeth A., et al. 2002. Photoprotective potential of lycopene, β-carotene, vitamin E, vitamin C and carnosic acid in UVA-irradiated human skin fibroblasts. *Free Radical Biology & Medicine* 32(12): 1293-1303.
Ames, Bruce N., et al. 2001. Delaying aging with mitochondrial micronutrients and antioxidants. *The Scientific World* 1: 81-82.
Arivazhagan, Palaniyappan, et al. 2001. Effect of DL-α-lipoic acid on mitochondrial enzymes in aged rats. *Chemico-Biological Interactions* 138: 189-198.

(Continued)

*Primary Examiner*—Gina C Yu
(74) *Attorney, Agent, or Firm*—Lydia G. Olson

(57) ABSTRACT

A topical composition comprising a lipoic acid, a carnitine, and a carnosine in a suitable vehicle for topical application and a method for treating skin is provided. The present compositions are useful in improving the appearance of aged skin characterized by wrinkles and loss of elasticity. Preferred components include R-lipoic acid or R-dihydrolipoic acid, acetyl-1-carnitine, and 1-carnosine.

24 Claims, No Drawings

OTHER PUBLICATIONS

Arrigoni-Martelli, E. and V. Caso. 2001. Carnitine protects mitochondria and removes toxic acyls from xenobiotics. *Drugs Exptl. Clin. Res.* XXVII(1) 27-49.

Hipkiss, Alan, R., et al. Carnosine, the anti-ageing, anti-oxidant dipeptide, may react with protein carbonyl groups. *Mechanisms of Ageing and Development* 122: 1431-1445.

Jeanmaire, C., et al. 2001. Glycation during human dermal intrinsic and actinic ageing: an in vivo and in vitro model study. *British Journal of Dermatology* 145: 10-18.

Atamna, Hani, et al. 2000. N-t-Butyl Hydroxylamine, a Hydrolysis Product of a-Phenyl-N-t-butyl Nitrone, Is More Potent in Delaying Senescence in Human Lung Fibroblasts. *The Journal of Biological Chemistry* 275(10): 6741-6748.

Hipkiss, A.R. and C. Brownson. 2000. A possible new role for the anti-ageing peptide carnosine. *Cell. Mol. Life Sci.* 57: 747-753.

Benathan, Messod, et al. 1999. Co-regulation of melanin precursors and tyrosinase in human pigment cells: roles of cysteine and glutathione. *Cellular and Molecular Biology* 45(7): 981-990.

Hagen, Tory M., et al. 1999. (R)-α-Lipoic acid-supplemented old rats have improved mitochondrial function, decreased oxidative damage, and increased metabolic rate. *FASEB J.* 13(2):411-418.

Kidd, Parris M., M.D. 1999. A Review of Nutrients and Botanicals in the Integrative Management of Cognitive Dysfunction. *Alternative Medicine Review* 4(33): 144-161.

McFarland, G.A. and R. Holliday, 1999. Further evidence for the rejuvenating effects of the dipeptide L-carnosine on cultured human diploid fibroblasts. *Experimental Gerentology* 34(1): 35-45.

Rebouche, Charles J. 1999. Carnitine. In Shils, M.E., et al., Eds. *Modern Nutrition in Health and Disease.* 9th Ed. Baltimore: Williams & Wilkins. 505-512.

Brass, Eric P., Ph.D. and William R. Hiatt, M.D. 1998. The Role of Carnitine and Carnitine Supplementation During Exercise in Man and in Individuals with Special Needs. *Journal of the American College of Nutrition* 1(3): 207-215.

Hagen, Tory M., et al. 1998. Acetyl-L-carnitine fed to old rats partially restores mitochondrial function and ambulatory activity. *Proc. Natl. Acad. Sci. USA* 95: 9562-9566.

Hagen, Tory M., et al. 1998. Mitochondrial Decay in Aging: Reversal through Supplementation of Acetyl-L-Carnitine N-tert-Butyl-α-phenyl-nitrone. *Ann. N.Y. Acad. Sci.* 854: 214-223.

Hipkiss, A.R., et al. 1998. Pluripotent Protective Effects of Carnosine, a Naturally Occurring Dipeptide, *Ann. N.Y. Acad. Sci.* 854: 37-53.

Hipkiss, Alan R. 1998. Carnosine, a protective, anti-ageing peptide? *The International Journal of Biochemistry and Cell Biology* 30: 863-868.

Hipkiss, Alan R. and Harj Chana. 1998. Carnosine Protects Proteins against Methylglyoxal-Mediated Modifications. *Biochemical and Biophysical Research Communications* 248: 28-32.

Ames, Bruce N., et al. 1995. Mitochondrial decay in aging. *Biochemica et Biophysica Acta* 1271: 165-170.

Maitra, Indrani, et al. 1995. α-Lipoic acid prevents buthionine sulfoximine-induced cataract formation in newborn rats. *Free Radical Biology& Medicine* 1(4): 823-829.

Pick, Uri, et al. 1995. Glutathione reductase and lipoamide dehydroganese have opposite stereospecificities for α-lipoic acid enantiomers. *Biochemical and Biophysical Research Communications* 206(2): 724-730.

Shigenaga, Mark K., et al. Oxidative damage and mitochondrial decay in ageing. *Proc. Natl. Acad. Sci. USA* 9: 10771-10778.

Quinn, P.J., et al. 1992. Carnosine: Its Properties, Functions and Potential Therapeutic Applications. *Moled. Aspects Med.* 13: 379-444.

Kohen, R., et al. 1991. The Sod Like Activity of Copper: Carnosine, Copper: Anserine and Copper: Homocarnosine Complexes. *Free Rad. Res. Commns.* 12-13: 179-185.

Gulyaeva, N.Y. 1987. Superoxide-scavenging activity of carnosine in the presence of $Cu^{2+}$ and $Zn^{2+}$. "*Biochemistry*" 52(7): 1216-1220 (abstract).

Benedetto, Jean-Pierre, et al. 1982. Role of Thiol Compounds in Mammalian Melanin Pigmentation. II. Glutathione and Related Enzymatic Activities. *The Journal of Investigative Dermatology* 769:422-424.

Benedetto, Jean-Pierre, et al. 1981. Role of Thiol Compounds in Mammalian Melanin Pigmentation: Part I. Reduced and Oxidized Glutathione, *The Journal of Investigative Dermatology* 77(5): 402-405.

Paglia, Donald E. and William N. Valentine. Studies on the quantitative and qualitative characterization of erythrocyte glutathione peroxidase, *The Journal of Laboratory and Clinical Medicine* 70: 158-169.

\* cited by examiner

TOPICAL FORMULATIONS AND METHODS OF USE

The present invention claims priority to U.S. Provisional Application No. 60/665,206 filed Mar. 24, 2005, herein incorporated by reference in it entirety.

FIELD OF INVENTION

The present invention relates to topical dermatological compositions and the topical application of such compositions for the prevention and/or treatment of damage to skin. This invention describes the application of topical compositions containing a lipoic acid, carnosine, and carnitine.

BACKGROUND OF THE INVENTION

Skin is subject to abuse by many extrinsic (environmental) factors as well as intrinsic factors. A common extrinsic factor is exposure to ultraviolet radiation. Whether extrinsic or intrinsic, the abuse results in skin aging. Skin aging happens in two ways: (1) through the natural aging process, which dermatologists call chronological aging (also known as chronoaging) and (2) through UV rays in sunlight accelerating the aging process, which doctors call photoaging. Chronoaging results in the thinning, loss of elasticity and general degradation of skin. As the skin naturally ages, there is a reduction in the cells and blood vessels that supply the skin. There is also a flattening of the dermal-epidermal junction, which results in weaker mechanical resistance of this junction. As a consequence, older persons are more susceptive to blister formation in cases of mechanical trauma or disease processes (Oikarinen et al., *Photodermatal. Photoimmunol. Photomed.*, 7:3-4 (1990)).

By contrast, photoaging, or premature aging, is a process in which the skin changes in appearance as a result of repeated exposure to sunlight. Typically, photoaging occurs in areas of habitual exposure, such as the scalp, face, ears, neck, chest, forearms, and hands. The changes associated with photoaging include elastosis, atrophy, wrinkling, vascular changes (diffuse erythema, ecchymoses, and telangiectasias), pigmentary changes (lentigines, freckles, and areas of hypo- and hyper-pigmentation), and the development of seborrheic keratosis, actinic keratosis, comedones, and cysts. Glycation has been seen to be enhanced in photoaged skin (Jeanmaire C. et al., *Br J Dermatol.* 2001 July; 145(1):10-8).

As skin ages, there is an increase in oxidative stress, an increase in inflammation, a decrease in collagen levels, overexpression of the enzyme MMP, an increase in protein glycation, and an increase in mitochondrial decay. Additional aging processes include the intrinsic rate of proton leakage across the inner mitochondrial membrane, decreased membrane fluidity, and decreased levels and function of cardiolipin. The mitochondria, which create the energy the cells need by converting dietary and other cellular fuels into ATP, are adversely affected by these aging processes. It has been shown that oxidants generated by mitochondria are the major source of the oxidative lesions in the mitochondria that accumulate with age. (Ames B N, et al., *Biochim Biophys Acta.* 1995 May 24; 1271(1):165-70). As the skin ages, the mitochondria become severely impaired, and this leads to both a decrease in ATP production and greater oxidative damage.

There are currently numerous compositions on the market for the prevention and/or treatment of aging skin for both chronoaging and photoaging. However, there still remains a need for an effective topical anti-aging formulation that can be used, without a prescription, to treat the effects of oxidation and other skin damage.

Antioxidants are known to be useful agents in compositions for treating the skin. Additionally, substances to treat mitochondrial energy are useful as agents for treating the skin. For example, compositions for increasing ATP production and thereby treating aging skin are known. These include the administration of acetyl-L-carnitine. However, this treatment is a double-edged sword, since the acetyl-L-carnitine, in addition to increasing the ATP production, also increases mitochondrial free radicals and causes oxidative damage to the mitochondria. The supplementation of rats with acetyl-L-carnitine, in addition to improving mitochondrial function and increasing general metabolic activity lowered the hepatocellular antioxidant status. (Liu J, et al., Ann N Y Acad Sci. 2002, 959:133-66; Hagen T M, et al. *Proc Natl Acad Sci USA* 2002; 99(4):1870-5; Hagen T M, et al. *Proc Natl Acad Sci USA* 1998; 95:9562-6).

The use of lipoic acid in topical formulations is known. Perricone describes the use of lipoic acid, which may be combined with other agents such as ascorbic acid, or α-hydroxy acid, (U.S. Pat. No. 6,752,999), or applied to the skin to treat inflammation (U.S. Pat. No. 5,709,868). Streicher, in U.S. Pat. Pub. 2003/0190337 describes the use of R-lipoic acid in a topical formulation. U.S. Pat. Pub. 2004/0265345 teaches the topical application of a composition containing acetyl carnitine and lipoic acid. U.S. Pat. Pub. 2004/0219114 discloses a composition containing an R-lipoic acid, coenzyme Q-10, and acetyl-L-carnitine hydrochloride.

Other combinations have been taught as useful oral supplements, but not as applied to topical formulations. For example, the combination of acetyl-1-carnitine and R-α-lipoic acid for oral treatment of mitochondrial decay and RNA/DNA oxidation was shown by Liu J, et al. in *Proc Natl Acad Sci USA* 2002; 99(4):2356-61, and the oral administration of acetyl-1-carnitine and lipoic acid to rats is known to improve metabolic function similar to the administration of acetyl-L-carnitine, but also decrease oxidative stress. (Hagen T M, et al. *Proc Natl Acad Sci USA* 2002; 99(4): 1870-5). The effects of feeding mitochondrial metabolites (acetylcarnitine and lipoic acid) and mitochondrial antioxidants (alpha-phenyl-N-t-butyl nitrone and N-t-butyl hydroxylamine) to rats on the age-associated mitochondrial decay of the brain has been shown to provide an improved age-associated decline of ambulatory activity and memory, partially restore mitochondrial structure and function and elevate the levels of antioxidants. (Liu J, et al., *Ann N Y Acad Sci.* 2002, 959:133-66). The combination of lipoic acid, acetyl-L-carnitine, and carnosine has been described as useful as an oral supplement for "longevity" by Tim Batchelder, LE Magazine September 2003 (www.lef.org/magazine/-mag2003/sep2003_report_alpha_01.htm).

However, a topical formulation combining the advantageous properties obtained from combining a lipoic acid, a carnitine, and a carnosine has not been described. Therefore, it is needed to provide topical formulations useful in treating and protecting the skin.

SUMMARY OF THE INVENTION

It is an object of the present invention to provide a method and composition for treating and protecting the skin.

In accordance therewith, a method and composition is provided for treating skin, comprising administering a topical composition to the skin, containing a lipoic acid, a carnitine, and a carnosine, or the dermatologically acceptable salt of any of these components in an amount effective to treat skin. Treating skin comprises treating skin damage and the signs of aging of the skin. The skin damage may be due to chronoaging or photoaging, and includes, for example, wrinkles, sagging skin, and decreased elasticity. Treating skin may also provide treatment of hyperpigmentation. One topical composition comprises R-lipoic acid and/or R-dihydrolipoic acid, acetyl-1-carnitine, carnosine, and a dermatologically acceptable carrier. Another embodiment of the invention provides a method for reducing mitochondrial decay in skin cells, comprising administering a topical composition to the skin, containing a lipoic acid, a carnitine, and a carnosine, or the dermatologically acceptable salt of any of these components in an amount effective to treat skin.

Additional agents such as NADH, an antioxidant, an AGE inhibitor, a collagen enhancing agent, a mitochondrial resuscitant, a light reflecting agent or a sunscreen, an anti-edemic agent, a glutathione or an inducers thereof, NADH, an anti-inflammatory agent, a phenylpropanoid glycoside, a depigmenting agent or agent addressing hyperpigmentation, a skin-protective lipids, hyaluronic acid, an alpha hydroxy acid, an agent useful for treating hormonal decline, an anti-acne agent, an agent altering lipolytic activity, an anti-cellulitic agent, an agent altering anti-capillary-fragility, an anti-elastase agent, an anti-erythema agent, or an agent that raises cyclic AMP may additionally be incorporated into the composition.

In a preferred embodiment, a liposome or similar carrier is used. This is useful in protecting the lipoic acid and other agents from oxidation before use.

Other features, advantages and embodiments of the invention will be apparent to those skilled in the art from the following description and appended claims.

DETAILED DESCRIPTION OF THE INVENTION

This invention is based upon the finding that a topical formulation containing an R-lipoic acid, a carnitine, and a carnosine or dermatologically acceptable salts thereof is particularly useful in treating the signs of aging on skin.

I. Lipoic Acid

A lipoic acid is a part of the topical formulation used in the present invention. Lipoic acid is described by:

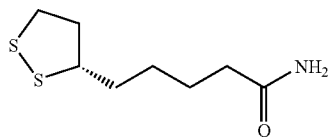

and is available in both the R and S forms. R-lipoic acid is a preferred form. The lipoic acid of the present invention also includes the reduced form, or dihydrolipoic acid (DHLA). In aqueous systems, both lipoic acid and DHLA show strong antioxidant activity. Lipoic acid has been shown to maintain microsomal protein thiols, protect against hemolysis, protect against neurological disorders, and protect against ischemia/reperfusion injury. Lipoic acid is also useful in treating diseases associated with oxidative stress including liver cirrhosis, atherosclerosis, and polyneuritis of diabetes mellitus. (Maitra, I., et al., *Free Rad. Biol. Med.* 18:823-829 (1995), introduction).

The antioxidative activity of lipoic acid is due, at least in part, to its ability to prevent free radical damage to cells and cell components. Free radical damage is most evident in cellular membranes because of the density of the molecular structure of the membranes. (R)-Lipoic acid has been shown to reverse the age-related decline in oxygen consumption and increase mitochondrial membrane potential. The age-related decline in hepatocellular glutathione and ascorbic acid levels is reversed by treatment with (R)-lipoic acid (as an oral supplement in rats). (Hagen T M, et al., FASEB J. 1999 February; 13(2):411-8).

R-lipoic acid is a mitochondrial antioxidant; it is implicated in mitochondrial energy production and protection from free radicals. R, not S-lipoic acid is produced by the body and decreases in concentration during the aging process (Pick U., et al., *Biochem Biophys Res Commun.* 1995 January 17; 206(2):724-30). The formulation of the present invention replenishes this vital substance as well as provides protection to the skin cells. R-lipoic acid is incorporated in the formulation in one preferred embodiment of the present invention.

The oral administration of lipoic acid to has been shown in rats, in combination with acetyl-1-carnitine, to improve metabolic function and decrease oxidative stress. The use of acetyl-1-carnitine alone was not sufficient. (Hagen T M, et al. *Proc Natl Acad Sci USA* 2002; 99(4):1870-5). (R)-Lipoic acid has also been shown to reverse the age-related decline in oxygen consumption and increase mitochondrial membrane potential. The age-related decline in hepatocellular glutathione and ascorbic acid levels is reversed by treatment with (R)-lipoic acid (as an oral supplement in rats). (Hagen T M, et al., FASEB J. 1999 February; 13(2):411-8).

Reduced R-lipoic acid, or R-dihydrolipoic acid (R-DHLA) may be used instead of lipoic acid. R-DHLA, which is formed in situ by the reduction of R-lipoic acid by NADH has more antioxidant properties than lipoic acid. Both DHLA and lipoic acid have metal-chelating capacity (LA chelates $Fe^{2+}$ and $Cu^{2+}$; DHLA chelates $Cd^{2+}$), and can scavenge reactive oxygen species. However, only DHLA can regenerate endogenous antioxidants and repair oxidative damage. DHLA can regenerate the endogenous antioxidants vitamin E, vitamin C and glutathione as well as provide peptide methionine sulfoxide reductase with reducing equivalents. The reducing equivalents help in the repair of oxidatively damaged proteins such as α-1 antiprotease. (Biewenga G P., et al., *Gen Pharmacol.* 1997 September; 29(3):315-31). DHLA is a potent sulfhydryl reductant and has also been shown to act as a strong direct chain-breaking antioxidant which may enhance the antioxidant potency of other antioxidants such as ascorbate and vitamin E. (Kagan V E, et al., *Biochem Pharmacol.* 1992 Oct. 20; 44(8):1637-49).

As used herein, the term "a lipoic acid" includes the R and S forms as well as racemic lipoic acid, DHLA, and dermatologically acceptable salts thereof. A combination of lipoic acids, such as R-lipoic acid and R-DHLA may also be used in the topical compositions of the present invention.

II. Carnitine

A carnitine is a part of the topical formulation used in the present invention. L-carnitine, the only biologically active isomer, (3-carboxylato-2-hydroxy-propyl)-trimethyl-ammonium, has the following chemical structure:

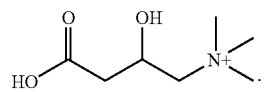

Carnitine is a betaine derivative required for the transport of long-chain fatty acids, ATP production, and removal of excess short- and medium-chain fatty acids. It is derived from the amino acid lysine and is also described as a β-hydroxy acid. Carnitine is a known staple of the cosmetic industry and is used for exfoliation and promoting cell renewal. Without the addition of other active agents, carnitine will also act, depending on the dosage, as an oxidant and can cause damage to the skin.

Acetyl-L-carnitine, more widely used than L-carnitine, enters cells and crosses the blood brain barrier more effectively than L-carnitine. (Kidd, P. M. 1999 *Alt. Med. Rev.* 4, 144-161). Propionyl-L-carnitine, which is not available in the US as an oral supplement, cleaves into L-carnitine and propionate, which is useful as an intermediate during energy metabolism (Brass E P, et al., *J Am Coll Nutr.* 1998; 17(3): 207-215).

As used herein, the term "a carnitine" includes L-carnitine, acetyl-L-carnitine, propionyl-L-carnitine, acetyl-L-carnitine arginate and dermatologically acceptable salts thereof (e.g., acetyl-L-carnitine hydrochloride and acetyl-L-carnitine arginate dihydrochloride). Additionally, the carnitine of the present invention may also be an amino carnitine. Amino carnitines are described in U.S. Pat. Nos. 6,953,865; 6,822,115; 6,528,684; 5,532,409; and 5,041,643 and include R(+)- and S(−)-aminocamitine chloride Acetyl-L-carnitine has a three pronged anti-aging effect by being a mitochondrial energy boosting agent, helping to boost acetyl-choline necessary for proper face muscle tone and being an effective antioxidant. It is useful in the transport of long-chain fatty acids into the mitochondrial matrix, transport of short- and medium-chain fatty acids away from the mitochondrial matrix, and regulation of energy metabolism through the modulation of acetyl CoA:CoA ratios. For this regulation, the acetyl group of acetyl CoA is transferred to L-carnitine by carnitine acetyl-transferase (CAT), freeing CoA to participate in the PDH reaction. The acetyl-L-carnitine can then be removed from the mitochondria. (Arrigoni-Martelli E, et al., *Drugs Exp Clin Res.* 2001; 27(1):27-49; Rebouche C J. Carnitine. In: Shils M E, et al. eds. *Nutrition in Health and Disease.* 9th ed. Baltimore: Williams & Wilkins; 1999:505-512). This increase of free CoA relative to acetyl CoA, enhances the activity of pyruvate dehydrogenase (PDH) which catalyzes the conversion of pyruvate to acetyl CoA, a crucial reaction in glucose metabolism. (lpi.oregonstate.edu/infocenter/othernuts/carnitine/carnitinerefs.html#ref2).

Particularly, carnitine is primarily an ATP increasing substance. Without the addition of other agents, carnitine will also act as an oxidant.

While meats, fish and dairy provide the richest sources of L-carnitine, it can also be found in tempeh (fermented soybeans), wheat, (0.1 mg/slice of bread), asparagus (0.4 mg/cup), and avocados (2 mg/ea). Generally, oral L-carnitine and acetyl-L-carnitine are available in doses from 500 mg to 2,000 mg/day (Hendler S S, Rorvik D R, eds. PDR for Nutritional Supplements. Montvale: Medical Economics Company, Inc; 2001), and the topical carnitine may be provided in similar or greater doses.

Acetyl-1-carnitine-arginate is described in U.S. Pat. No. 5,270,472 and has been shown to stimulate the growth of neurites in the brain by as much as 19.5 percent, similar to the stimulating effect of nerve growth factor itself. Acetyl-L-carnitine arginate can act acts with acetyl-L-carnitine to increase neurite growth. (Taglialatela G, et al., *Neurochem Res* 1995 January; 20(1):1-9).

III. Carnosine

A carnosine is a part of the topical formulation used in the present invention. Carnosine, the dipeptide β-alanyl-L-histidine, and its related compounds such as anserine (β-alanyl-1-methyl-L-histidine) and homocarnosine (γ-amino-butyryl-L-histidine) are present in millimolar concentrations in tissues, including skeletal muscle and brain. Carnosine is an antioxidant, an anti-glycation agent, and a free radical scavenger. Carnosine is also known as a carbonyl trap. Additionally, the part of the mitochondria that is more susceptible mitochondrial lipid peroxidation (malondialdehyde, MDA) can be protected by carnosine.

As used herein the term "a carnosine" encompasses the dipeptide β-alanyl-L-histidine; it includes D,L-carnosine, D-carnosine, L-carnosine, the derivatives anserine and homocarnosine, as well as their salts, such as zinc carnosine, copper carnosine, and copper anserine. (Hipkiss A R, Chana H, *Biochem Biophys Res Commun.* 248(1):28-32, 1998; Hipkiss A R et al., *Ann N Y Acad Sci,* 854:37-53, 1998); Carnosine has been shown to possess strong and specific antioxidant properties. It is a potent anti-glycation agent and has unique anti-aging properties. It also promotes wound healing (Roberts P R, et al., *Nutrition* 1998; 14; 266-9), protects against radiation damage, is potentially a modulator of enzymatic activities, and has been shown to be a chelator of heavy metals. (Quinn, P J et al., *Mol. Aspcts Med.* 1992; 13(5), 379-444; (Hipkiss A R. *Int J Biochem Cell Biol* 1998; 30:863-8). Carnosine is degraded by histidine and carnosinase to form histamine and β-alanine. (Nagai, K et al., *Surgery* 1986, 100(5); 815-821). The β-alanine produced by the degradation of carnosine stimulates the biosynthesis of nucleic acids and of collagen. This increased collagen synthesis is an important aspect of the present invention, as it provides additional benefit to the skin and reduces the effects of aging. Similarly, the histamine produced by the degradation process stimulates early effusion at the initial stage of tissue inflammation. Researchers have hypothesized that the effectiveness of carnosine stems from its ability to react with carbonyl groups on glycated or oxidized proteins (i.e., carnosinylation); this reaction inhibits the glycoxidised proteins from cross-linking with normal macromolecules and causing the signs of aging. (Hipkiss A R, et al., *Mech Ageing Dev* 2001 Sep. 15; 122(13): 1431-45; Hobart et al. *Life Sci.* 75:1379-89).

The salts and derivatives of carnosine are also useful additions to the present invention and salts and derivatives thereof, which function as a pH buffer and also act as an agent of inhibiting protein cross-linking. One preferred embodiment uses N-acetyl-carnosine as it is highly resistant to hydrolysis by carnosinases and therefore may provide protection from AGEs for a longer period of time in comparison to carnosine. Zinc and copper complexes of carnosine are also useful as chelating agents (Kohen et al., Free *Radic. Res. Commun.* 991; 12-13 Pt 1:179-85).

Carnosine reacts strongly with aldehyde and keto groups of sugars by Amadori reaction, and is also theorized to deplete certain glycolysis intermediates. Therefore, a reduction of glycolysis intermediates by carnosine depletes their energy supply. But the addition of pyruvate reverses this effect. (Holliday R *Br J Cancer.* 1996 April; 73(8):966-71). Therefore, in one embodiment, it is preferable to add carnosine in a formulation with an agent which also reduces the amount of pyruvate available. Additionally, the reaction between carnosine and aldehydes protects susceptible macromolecules. Therefore, carnosine inhibits nonenzymic glycosylation and cross-linking of proteins induced by reactive aldehydes (aldose and ketose sugars, certain triose glycolytic intermediates and malondialdehyde (MDA), a lipid peroxidation product). (Hipkiss A R, et al., *Ann N Y Acad Sci.* 1998 Nov. 20; 854:37-53).

Carnosine has also been shown to be beneficial on growth, morphology, and longevity of cultured human fibroblasts, and has an important role in cellular homeostasis and maintenance. (McFarland G A, et al, *Exp Gerontol*. 1999 January; 34(1):35-45). Camosine ALSO functions as a pH buffer and also acts as an agent of inhibiting protein cross-linking (Hobart et al. *Life Sci.* 75:1379-89). Zinc and copper complexes of carnosine are also useful as chelating agents (Kohen et al., *Free Radic. Res. Commun.* 991; 12-13 Pt 1:179-85).

Carnosine is also useful in that it is an inhibitor of matrix metalloprotease (MMP). Carnosic acid has been seen to suppress metalloproteinase 1 (MMP-1) concentration in human skin fibroblasts. (Offord E A, et al., Free Radic Biol Med. 2002 June 15; 32(12):1293-303). This is particularly useful since MMP is overexpressed as the skin ages. (Ames B N, et al., *Biochim BiophysActa*. 1995 May 24; 1271(1):165-70).

When carnosine is chelated to zinc or copper ions, the presence of the ions enhances camosine's activity as a superoxide radical scavenger (Gulyaeva N Y, *Biochemistry* 57 (7:2) 1051-4, 1987). Therefore, the addition of camosine as an agent in the present invention in chelated form provides for superoxide scavenger activity as well as the anti-glycation and anti-oxidation properties of carnosine. Carnosine has been administered at dosages above 500 mg/kg body weight in animal studies and has found to be safe.

IV. Combinations

The topical formulation of this invention, containing a combination of a lipoic acid, a carnosine, and a carnitine, is particularly advantageous because of the multi-pronged effect these ingredients have for addressing the aging process. Each of R-lipoic acid, L-carnitine, and carnosine are produced by the body and their secretion generally decrease with age, and the topical application of these or related compounds provides protection against loss due to age. They are also all effective antioxidants, dependent on the dosage.

The efficacy of a composition containing a lipoic acid, a carnosine, and a carnitine for treating aging skin is greater than that of a composition containing only one or two of these agents because the formulation addresses three major causes of skin aging: 1) oxidative damage (lipoic acid, and also carnosine) 2) mitochondrial decline/ATP production (carnitine, and also lipoic acid), and 3) glycation of proteins through reactive carbonyl species (carnosine). Therefore, the lipoic acid, carnosine, and carnitine formulation accomplishes vital functions in protecting the skin, it quenching free radicals, provides mitochondrial resuscitation, and neutralizes the damage caused by glycation.

A particular advantage of the formulation of the present invention is the synergy between the components of the formulation in acting on the mitochondria. Carnitine, and to some extent R-lipoic acid, boost the production of ATP in the skin. However, mitochondria, in addition to enhancing ATP production and making the skin appear younger, generates oxygen radicals and hydrogen peroxide, and is susceptible to oxidative stress. (Hardman D. J. Am. Geriatr. Soc. 20: 145-147, 1972). The addition of the mitochondrial antioxidant R-lipoic acid, reduces or counters the oxidative effect of the carnitine. Therefore, without the advantages provided by the formulation described herein, the benefits gained by an increase in ATP is counteracted by the increased oxidative stress.

This effect is similar to that shown to occur for the dietary supplementation using acetyl-L-carnitine to increase cellular respiration, mitochondrial membrane potential, and cardiolipin values where PBN was administered to lowered oxidant production to improve mitochondrial function without a significant increase in oxidative stress. (Hagen T M, Wehr C M, Ames B N, *Ann N Y Acad. Sci.* 1998; 854:214-23). Similarly, the addition of a mitochondrial antioxidant, which is a free radical scavenger, reduces or prevents this oxidative damage.

If a carnitine (i.e., acetyl-L-carnitine) were used on its own, it would act primarily as an ATP increasing agent with the additional oxidative activity on the mitochondria, thereby causing oxidative stress to the mitochondria. This is particularly true if given in high doses. High doses of carnitine are also known to produce additional carbonyl species (Liu et al., *Ann. NY AcadSci* 959:133-166 (2002). The combination of a carnitine with a mitochondrial antioxidant (i.e., a lipoic acid such as R-DHLA) reduces the oxidative damage of the carnitine and effectively reduces the signs of aging and mitochondrial decay in the skin. Additionally, since carnosine is known to prevent carboxylation of proteins, the combination prevents the formation of these highly active moeitys.

Additionally, the carnosine in the formulation is particularly effective at scavenging certain free radicals, especially free radicals formed in the process of glycation, which are not reduced as effectively by other antioxidants.

Each of these agents, used on their own, may require a percentage that is high enough to create to create a size effect. If a lipoic acid were used on its own, it would behave as an irritant to the skin. Similarly, if a carnosine were used on its own, it could cause an unwanted inflammatory action. Carnitine would act as an oxidant. The combination of a lipoic acid with a carnitine and carnosine reduces these effects.

Further, in some embodiments of the present invention, the formulation will also include an additional mitochondrial resuscitant. This increases the antioxidation effectiveness of the formulation in the mitochondria as well as decreases formulation cost. Particularly useful mitochondrial resuscitants are sugars such as R-ribose. These agents also are glycating agents and can adversely affect the skin. However, the carnosine present in the formulation will act as an anti-glycation agent and prevent this adverse effect.

Therefore, the formulation of the present invention provides a means to combat aging by quenching free radicals, slowing or reversing mitochondrial energy decline, and inhibiting the production of AGEs. Additionally, DHLA regenerates endogenous antioxidants and is a strong direct chain-breaking antioxidant; acetyl-L-carnitine helps to boost acetylcholine which aids in muscle tone and aids in energy metabolism; and carnosine is a chelator of heavy metals and stimulates the biosynthesis of collagen. The combination of these three compounds is superior to a combination of only two compounds or other anti-aging topical formulations because of the strong antioxidant effect in combination with the different activities of the lipoic acid, carnitine, and carnosine.

The compounds of the present invention are preferably in the pure stereoisomers: 1-carnosine, acetyl-1-carnitine (manufactured by Lonza for example) and R-lipoic/R-dihydro-lipoic acid.

Formulating the compounds described herein in a liposome or other microencapsulation carrier adds still further benefit to the present invention because the encapsulation reduces the exposure to oxidants and thereby prolongs the antioxidant activity of the components.

In one embodiment, two or more of the active agents are chemically linked to each other, either directly or through a linker such as an alkyl chain or those described for aminocarnitines. For example, lipoic acid may be bonded to carnitine, or carnosine may be bonded to lipoic acid. These agents will be linked using methods known in the art and tested to make sure they maintain their activity.

The formulation will preferably comprise a lipoic acid or a dermatologically acceptable salt thereof in an amount of from about 0.01 to 50% by weight, based on the total weight of the composition, or more preferably in an amount of from about 0.1 to 7.0% by weight, based on the total weight of the composition. The formulation will preferably comprise a carnitine or a dermatologically acceptable salt thereof in an amount of from about 0.01 to 50% by weight, based on the total weight of the composition, or more preferably in an amount of from about 0.5 to 2.0% by weight, based on the total weight of the composition. The formulation will preferably comprise carnosine or a dermatologically acceptable salt thereof in an amount of from about 0.01 to 50% by weight, based on the total weight of the composition, or more preferably in an amount of from about 0.1 to 5.0% by weight, based on the total weight of the composition. The formulation of claim 22, which comprises component (i) in an amount of from about 0.5 to 2.0% by weight, component (ii) in an amount of from about 0.5 to 2.0% by weight, and component (iii) in an amount of from about 0.1 to 5.0% by weight, based on the total weight of the composition.

V. Additional Agents

In addition to the lipoic acid, carnosine, and carnitine, many preferred embodiments of this invention contain at least one or more other active ingredients. A non-limiting list of such ingredients includes the following.

The additional agents can be used alone in the formulation of the present invention, or may be in the form of mixtures. The amount of additional agent is dependent upon the activity of that particular agent, and will vary depending upon the preferred formulation. Other than as specifically provided herein, each agent will be present in the formulation in an amount from about 0.001 to about 30% by weight, preferably from about 0.1 to about 5% by weight, based on the total weight of the preparation.

Antioxidants

In particular, preferred embodiments of the additional active ingredients included in the compositions of the present invention are compounds having antioxidative action. Exemplary antioxidants include, but are not limited to, amino acids (e.g. glycine, histidine, tyrosine, and tryptophan) and their derivatives, imidazoles (e.g. urocanic acid) and their derivatives, carotenoids (e.g. lutein, lycopene), carotenes (e.g. α-carotene, β-carotene, lycopene, canthaxantin, cryptoxanthin, zeaxanthin and astaxanthin) and their derivatives, chlorogenic acid and its derivatives, aurothioglucose, propylthiouracil, thiotaurine and other thiols (e.g. thioredoxin, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, aminoethylcysteine, decarboxylated dimmer of aminoethylcysteine ketimine, dilauryl thiodipropionate, distearyl thiodipropionate, thiodipropionic acid and their derivatives (esters, ethers, peptides, lipids, nucleotides, nucleosides and salts) and sulphoximine compounds (e.g. buthionine sulphoximines, homocysteine sulphoximine, buthionine sulphones, pentathionine sulphoximine, hexathionine sulphoximine, heptathionine sulphoximine) in very low, acceptable doses (e.g. pmole to µmoles/kg); also (metal) chelating agents (e.g. α-hydroxy fatty acids, palmitic acid, phytic acid, lactoferrin, tannins, and curcumine), α-hydroxy acids (e.g. citric acid, lactic acid, malic acid, mandelic acid), humic acid, colic acid, colic extracts, bilirubin, biliverdin, EDTA, EGTA and their derivatives, unsaturated fatty acids and their derivatives (e.g. γ-linolenic acid, linolic acid, oleic acid), folic acid and their derivatives, ubiquinone and ubiquinol and their derivatives, vitamin A and derivatives (e.g. vitamin A palmitate), the B vitamins and their derivatives, coniferyl benzoate of benzoin resin, rutinic acid and their derivatives, butylhydroxy toluene, butylhydroxy anisole, nordihydroguaiacic acid, nordihydroguaiaretic acid, trihydroxybutyrophenone, uric acid and its derivatives, mannose and its derivatives, sesamol, sesamolin, zinc and its derivatives (e.g. ZnO, $ZnSO_4$) including zinc amino acid chelates (zinc-methionine, zinc acetylmethionate), selenium and its derivatives (e.g. selenium methionine), stilbenes and their derivatives (e.g. stilbene oxide, trans-stilbene oxide), proanthocyanidins, ascorbic acid, particularly fat-soluble fatty acid esters of ascorbic acid (e.g. ascorbyl palmitate and tetrahexydecyl ascorbate), quercetin and its derivatives (e.g. quercetin glycoside or rutin), hesperidine, sylimarin, sylibin, glabridin, superoxide dismutase and their derivatives, catalase and its derivatives, carnosic acid and its derivatives, apigenin and its derivatives, luteolin and its derivatives, chlorogenic acid and its derivatives, caffeic acid and its derivatives, ferrulic acid and its derivatives, resveratrol and its derivatives, green tea polyphenols and its derivatives, matrix metalloproteinase inhibitors (e.g. green tea polyphenols, trans-retinoic acid, luteoline, quercetine, ursolic acid, shark cartilage preparations, diterpenes and ursolic acid from *Siegesbeckia* and *Centaurium* extracts, and a tocopherol), Coenzyme Q10, glutathione and its derivatives, myristicin, changkil saponins (from *platycodon grandiflorium*, which is also known as jie geng), pomengranate, ellagic acid, honokiol (from *magnolia officinalis*), magnolol (from *magnolia officinalis*), naringenin, clove essential oil, martynosides, verbascosides, wolfberry (from *lycium barbarum*) extracts, cascading antioxidants including but not limited to carnosic acid, standardized extract of *Phyllanthus emblica* (trade named *Emblica*), *pinus maritima* and *pinus radiata* bark extracts, hydroxytyrosol (from olives), genistein, thiotaurine, antioxidants from marine species (e.g., Bioplasma® and monostrama extract from Secma), roxisomes (from AGI), crocetin, pine pollen extracts, beta glucans and the suitable derivatives of the invention (salts, esters, ethers, sugars, nucleotides, nucleosides, peptides and lipids) of these said active ingredients.

Anthocyanins and their derivatives are particularly preferred antioxidants. Anthocyanins encompasses a class of flavonoid compounds that are naturally occurring, water-soluble compounds, responsible for the red, purple, and blue colors of many fruits, vegetables, cereal grains, and flowers. Anthocyanins are susceptible to degradation by light, heat, oxygen, and other reactants including iron, copper, and tin. The antioxidant properties of the anthocyanins can be measured by their capacity to absorb free radicals. The oxygen radical absorbance capacity (ORAC) is a measurement of this. Anthocyanins generally have a high ORAC rating compared to other antioxidants. Further, for ripe berries, there is a linear relationship between ORAC values and anthocyanin content. High ORAC ratings include 25-200 µmole of Trolox equivalents (TE)/g. In most fruits (i.e., not just the fruits with high anthocyanin content), ORAC values ranged from 7.8 to 33.7 µmole TE/g g of fresh berries and the ORAC values of the leaves range from 69.7 to 182.2 µmole TE/g. (Wang S Y, Lin H S., *J Agric Food Chem.* 2000 February; 48(2):140-6). Black raspberries have a very high ORAC of 77 µmole TE/g while boysenberries have an ORAC of 48 µmole TE/g and red raspbererries and blueberries have 24 and 23 µmole TE/g respectively. (http://www.deckerfarm.com/anti-oxidants.html). Acai is another fruit having a high ORAC content. The stage at which the plant is harvested affects the ORAC value. Blackberries have their highest ORAC values during the green stages, whereas red raspberries have their highest ORAC values when ripe. In one embodiment, the antioxidant is selected from a natural product having a high ORAC value.

The ORAC may be obtained by using the method described by the U.S. Department of Agriculture's Agricultural Research Service (Prior and Cao, 83(4) J. AOAC INT. 950-6 (2000)). Additionally, testing for ORAC, H-ORAC, N-ORAC, S-ORAC, and ORAC-E (high throughput ORAC for oil-in-water emulsion) are available from Brunswick Laboratories (www.brunswicklabs.com).

Additionally, anthocyanins are collagenase inhibitors. The inhibition of collagenase helps in the prevention and reduction of wrinkles, increase in skin elasticity, etc., which are caused by a reduction in skin collagen.

The anthocyanins useful in the present invention may be obtained from any portion of various plant sources, such as the fruit, flower, stem, leaves, root, bark, or seeds. One of skill in the art will understand that certain portions of the plant may contain higher natural levels of anthocyanins, and, therefore, those portions are preferably used to obtain the desired anthocyanins. Methods to determine whether and which portions of a plant contain anthocyanins are known and not discussed herein. The extraction and identification of various anthocyanins are described, for example, in U.S. Pat. No. 6,818,234, U.S. Pat. No. 6,780,442, and U.S. Pat. No. 4,413,004.

Particularly preferred anthocyanins are derived from natural sources having high anthocyanin content. Approximately 300 anthocyanins have been discovered in nature, and come from sources including, but not limited to: acai berries, aronia berries, apples, bilberries, black carrots, blueberries, cherries, cranberries, eggplants, elderberries, grapes, purple carrots, purple loosestrife, purple rice, radishes, raspberries, red cabbage, redcurrants, red-fleshed potatoes, red raspberries, red onions, species from the Rubus class (e.g, black raspberry, blackberry, and youngberry), species from the Ribus class (e.g., black currant and gooseberry), sea buckthorn, wolfberry extract, and strawberries. One particularly preferred anthocyanin is aronia berry due to it high ORAC. Wild blueberry is another particularly preferred anthocyanin having a high ORAC that may be added to the formulation of the present invention.

Other preferred anthocyanins used in the topical formulation of the present invention are formed from a combination of two or more (i.e., 2, 3, 4, 5, or 6) different sources of anthocyanins. For example, an embodiment may include anthocyanins derived from both aronia berry and from youngberry.

When anthocyanins are used, flavonoid glucuronides and flavonoid glycuronides may be added to the formulation of the current invention as a stabilizer for one or more anthocyanin. As used herein, the term "flavonoid glucuronide" encompasses flavonoids that are attached to a glucuronic acid (e.g., glucose having a carboxylic acid at the C6 position on the sugar ring); the term also encompasses flavonoid glucosides, which are flavonoids attached to glucose. Similarly, flavonoid glycuronides are flavonoids attached to glycuronic acid, and flavonoid glycosides, which are herein encompassed in the term flavonoid glycuronides, are flavonoids attached to a glycose. One particularly useful flavonoid glucuronide is the glucuronide derived from rosemary. Other exemplary flavonoid glucuronides can be found in U.S. Pat. No. 5,908,650

In one embodiment, additional antioxidant included in the compositions of the present invention is one or more betacyanin. Betacyanins, like anthocyanins, may be obtained from natural sources and are antioxidants. One betacyanin of interest is betanin found in beets.

Retinol and its derivates such as retinyl palmitate and trans-retinoic acid as well as retinols stabilized in liposomes and cyclodextrin preparations may be added to the present invention. One retinol derivate of interest is tocopheryl-retinoate available from Nikko Chemicals Co. LTD.

Vitamin C and derivatives including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, *emblica officinalis*, and bioflavonoids from rose hip and citrus may be used including watersoluble bioflavonoids such as hesperidin methyl chalcone.

In another embodiment, the antioxidant is superoxide dismutase (and derivatives), catalase (and derivatives), or a mixture thereof. In a particularly advantageous embodiment SOD is heterologous SOD (HSDs) described in U.S. Pat. No. 6,426,068, which no longer, or practically no longer, exhibit dismutase activity, but which have conserved their immunoredox activity, stimulate the production of endogenous SOD, as well as the production of catalase and of glutathione peroxidase. According to another advantageous embodiment of said use, said plant heterologous SOD is in particular derived from melon. The prefered embodiment uses an encapsulated SOD.

Sesame (*Sesamum indicum*) or sesame lignan may also be added to the present invention. Sesame and its lignans (the fibrous compounds associated with the sesame) act as antioxidants, reduce inflammation, normalize blood pressure, improve lipid levels, and promote fat burning. Sesame has also been show to aid in the oxidation power or bioavailability of fish oil, and conjugated linoleic acid and enhances the anti-inflammatory effects of essential fatty acids, lower total cholesterol and low-density lipoprotein (LDL), block oxidative damage implicated in atherosclerosis, and reduces blood pressure. Sesame lignans can dramatically increase tissue and serum levels of the vitamin E fractions $\alpha$ tocopherol and $\gamma$ tocopherol, thereby enhancing their protective properties. (Yamashita K, et al., *J Nutr.* 1992; 122(12):2440-6). Studies have shown that sesame can also reduce inflammatory processes known to promote cancer, senescence, and aging.

Sesame seed lignans significantly enhance vitamin E activity and increase a tocopherol concentrations in the blood and tissue of rats fed a diet containing a tocopherol and sesame seed or its lignans. (Yamashita K, et al., *Lipids.* 1995 December; 30(11):1019-28). Additionally, they elevate gamma tocopherol concentration by inhibiting an enzyme involved in breaking down tocopherols and tocotrienols. (Ikeda S, et al., *J Nutr.* 2002 June; 132(5):961-6).

Other preferred antioxidants, which may be incorporated in the compositions of the present invention include tocopherols (e.g. d-$\alpha$-tocopherol, d-$\beta$-tocopherol, d-$\gamma$-tocopherol, d-$\delta$-tocopherol), tocotrienols (e.g. d-$\alpha$-tocotrienol, d-$\beta$-tocotrienol, d-$\gamma$-tocotrienol, d-$\delta$-tocotrienol,) and vitamin E ($\alpha$-tocopherol acetate). These compounds added to the compounds of the present invention may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. The increased glutathione peroxidase activity protects the skin from oxidative damage. (Musalmah M, et al., Asia Pac *J Clin Nutr.* 2002; 11 Suppl 7:S448-51).

Gamma tocopherol is one particularly advantageous E vitamin since it is capable of quenching reactive nitrogen oxide species such as peroxynitrite and nitrogen dioxide. (Boje K M. *Front Biosci.* 2004 Feb. 1; 9:763-76). Gamma tocopherol and its water-soluble metabolite, gamma-CEHC have been shown to reduce inflammation by inhibiting prostaglandin E2 (Jiang Q, et al., *Proc Natl. Acad Sci USA.* 2000 Nov. 10; 97(21):11494-9) and gamma tocopherol administration correlates with a reduced risk from heart disease. (Kushi L H, et al. *N Engl J Med.* 1996 Jun. 2; 334(18):1156-62).

When a tocopherol or tocotrienol is added to the formulation of the present invention, it is also preferably to add sesame oil (or an extract thereof such as sesaminol, a sesame lignans) due to the enhanced antioxidant effect of the combination. (Ghafoorunissa, Hemalatha S., et al., *Mol Cell Biochem.* 2004 July; 262(1-2):195-202; Yamashita K, et al., Lipids. 2002 April; 37(4):351-8). One preferred formulation contains d-α-, d-β-, d-γ-, and d-δ-tocopherol, d-α-, d-β-, d-γ-, and d-δ-tocotrienol in addition to the sesame lignans. Gamma-tocopherol, followed by δ and α tocopherol has the highest content, with a reduced risk from heart disease. (Kushi L H, et al. *N Engl J Med.* 1996 June 2; 334(18):1156-62).

Vitamin A is a preferred addition to formulations of the present invention because of the increased stability it can impart to lipoic acids. Segall, A., *J Cosmet Sci.* 2004 September-October; 55(5):449-61.

In addition, carotenoids, particularly the xanthophyll type, are also preferred antioxidants that can be used in the practice of the instant invention. The xanthopyll type carotenoids include molecules, such as lutein, canthaxantin, cryptoxanthin, zeaxanthin and astaxanthin. Xanthophylls protect compounds, such as vitamin A, vitamin E and other carotenoids (Demmig-Adamas, B. *Biochemica et Biophsyica Acta,* 1020: 1-24 (1990)). Xanthophylls can be obtained from a multitude of natural sources, or produced as described, for example, in U.S. Pat. No. 5,916,791.

Flavan-3-ols are also preferred antioxidants that may be used in the formulations of the present invention; they belong to a class of nutrients known as the flavonoid family. Particularly preferred flavan-3-ols include the procyanidin mixtures extracted from grape (*Vitis vinifera*) seed. Proanthocyanidins play a role in the stabilization of collagen and maintenance of elastin, two critical proteins in connective tissue that support organs, joints, blood vessels, and muscle (Mitcheva et al. *Cell Mol Bio* 39:443-8 (1993) and Maffei et al. *Arzneimittelforschung;* 44:592-601 (1994)). Possibly because of their effects on blood vessels, proanthocyanidins have been reported in double-blind research to reduce the duration of edema after face-lift surgery from 15.8 to 11.4 days (Baroch et al. *Ann Chir Polast Esthet* 29:393-5 (1984)). Other flavan-3-ols may also be added to the composition. These include catechin and epicatechin. Procyanidins are the dimers and oligomers of catechin and epicatechin and their gallic acid esters, and are widely distributed in the plant kingdom. Other flavonoids, such as isoflavin β, quercetin, glabridin, red clover, and others described in U.S. Pat. Nos. 5,686,082 and 5,686,367 may also be included in the composition.

Additional antioxidants that may be used in the topical formulation of the present invention include the antioxidants provided in Table I

TABLE I

| | | | |
|---|---|---|---|
| (+)-catechin | catechol | hydroxy-chavicol | polyphenols |
| (+)-gallocatechin | celestrol | hyperin | pomiferin |
| (+)-syringaresinol | cepharanthine | hyperoside | proanthocyanidins |
| (−)-bisparthenolidine | chamazulene | ionol | procyanidin-a-2 |
| (−)-bornyl-caffeate | chlorogenic-acid | isochlorogenic-acid | procyanidin-b-2-3'-o-gallate |
| (−)-bornyl-ferulate | chlorophorin | isoeugenol | procyanidin-b-2-3,3'-di-o-gallate |
| (−)-bornyl-p-coumarate | chlorophyll | isoferulic-acid | procyanidin-b-5-3,3'-di-o-gallate |
| (−)-epicatechin | cholesterol | isofraxin | procyanidin-c-1-3,3',3''-tri-o-gallate |
| (−)-epicatechin-3-o-gallate | chrysoeriol | isoorientin | procyanidins |
| (−)-epigallocatechin | cimicifugic-acid-a | isopiline | propyl-gallate |
| (−)-epigallocatechin-3-o-gallate | cimicifugic-acid-b | isoquercitrin | protocatechualdehyde |
| (−)-epigallocatechin-gallate | cimicifugic-acid-f | isorhamnetin | protocatechuic-acid |
| (−)-hydroxyjasmonic-acid | cimiracemate-a | isorhamnetin-3,7-di-o-β-d-glucopyranoside | protopapaverine |
| (1's)-1'-acetoxychavicol-acetate | cimiracemate-b | isorhamnetin-diglucoside | prunusol |
| (2r)-(12z,15z)-2-hydroxy-4-oxoheneicosa-12,15-dien-1-yl-acetate | cis-10-heptadecenoic-acid | isorosmanol | pterostilbene |
| (7r,10r)-carota-1,4-dienaldehyde | cis-10-nonadecenoic-acid | isoterchebin | puerarin |
| 1,2,6-tri-o-galloyl-beta-d-glucose | cis-10-pentadecenoic-acid | isothymonin | punicacortein |
| 1,7-bis(3,4-dihydroxy-phenyl)hepta-4e,6e-dien-3-one | cis-11,14-eicosadienoic-acid | isothymusin | purpurogallin |
| 1-o-(2,3,4-trihydroxy-3-methyl)-butyl-6-o-feruloyl-beta-d-glucopyranoside | cis-11-eicosenoic-acid | isotorachrysone | pycnogenol |
| 2,3,7-trihydroxy-5-(3,4-dihydroxy-e-styryl)-6,7,8,9-tetrahydro-5h-benzocycloheptene | cis-11-vaccenic-acid | isovitexin | pyrocatechol |

TABLE I-continued

| | | | |
|---|---|---|---|
| 2-(3',4-diphenyl)-ethanol | cis-13,16,19-docosatrienoic-acid | kaempferol | pyrogallol |
| 2-caffeoyl-oxy-3-{2-(4-hydroxybenzyl)-4,5-dihydroxy}phenylpropionic-acid | cis-13,16-docosadienoic-acid | kaempferol-3-o-α-arabinopyranoside-2''-gallate | quercetagenin-7-o-glucoside |
| 3',4',5,7-tetrahydroxyflavone | cis-13-erucic-acid | kaempferol-3-o-α-l-rhamnopyranosyl-(1->6)-β-d-glucopyranoside | quercetagetin |
| 3,3'-dimethylellagic-acid | cis-15-nervonic-acid | kaempferol-3-o-β-d-glucopyranosyl-(1->2)-[α-l-rhamnopyranosyl-(1->6)-β-d-galactopyranoside | quercetin |
| 3,4,5-tri-o-caffeoylquinic-acid | cis-8,11,14-eicosatrienoic-acid | kaempferol-3-o-galactoside | quercetin-3,4'-diglucoside |
| 3,4-dicaffeoyl-quinic-acid | cis-9,12,15-linolenic-acid | kaempferol-7-o-rhamnoside | quercetin-3-o-α-arabinopyranoside-2''-gallate |
| 3,4-dihydroxybenzoate | cis-9,12-linoleic-acid | l-alanine | quercetin-3-o-α-l-rhamnopyranosyl-(1->6)-β-d-glucopyranoside |
| 3,4-hydroxycinnamic-acid | cis-9-oleic-acid | l-glutathione | quercetin-3-o-β-d-glucopyranoside |
| 3,5,8,3',4'-pentahydroxyflavone | cis-9-palmitoleic-acid | labiatic-acid | quercetin-3-o-β-d-glucopyranosyl-(1-->6)-β-d-glucopyranoside |
| 3,5-di-o-caffeoylquinic-acid | citrifolinin-b | laudanosoline | quercetin-3-o-β-d-glucopyranosyl-(1->2)-α-l-rhamnopyranosyl-(1->6)-β-d-galacopyranoside |
| 3,5-dicaffeoyl-quinic-acid | clausenamide | lauric-acid | quercetin-4'-β-glucoside |
| 3,7,8,2',5'-pentahydroxyflavone | cleomiscosin-c | lauryl-gallate | quercetin-4'-glucosyl-gallate |
| 3-beta-23,28-trihydroxy-12-oleanene-23-caffeate | coclaurine | leucoanthocyanin | quercetin-4'-o-β-d-glucopyranoside-6''-gallate |
| 3-beta-23,28-trihydroxy-12-oleanene-3-beta-caffeate | coniferyl-alcohol | lignans | quercitrin |
| 3-beta-trans-(3,4-dihydroxycinnamoyloxy)-20(29)-lupen-28-oic-acid | corilagin | lignin | resorcinol |
| 3-beta-trans-(3,4-dihydroxycinnamoyloxy)-olean-12-en-28-oic-acid | corypalmine | linalyl-acetate | resveratrol |
| 3-beta-trans-(3,4-dihydroxycinnamoyloxy)-olean-18-en-28-oic-acid | crocetin | lupeol | rhamnetin |
| 3-hydroxy-flavone | curcumin | lupulone | robinetin |
| 3-o-caffeoylquinic-acid | cyanidin | lutein | robinin |
| 4,5-di-o-caffeoylquinic-acid | cyanidin-3,5-diglycoside | luteolin | rosmadial |
| 4-acetylarabinosyl-ellagic-acid | cyanidin-3-o-β-d-glucoside | luteolin-3'-o-(3''-o-acetyl)-β-d-glucuronide | rosmanol |
| 4-acetylxylosyl-ellagic-acid | cyanidin-3-o-galactoside | luteolin-3'-o-(4''-o-acetyl)-β-d-glucuronide | rosmanol-9-ethyl-ether |
| 4-allyl-pyrocatechol | cyanidin-3-rutinoside | luteolin-4'-o-glucoside | rosmaridiphenol |
| 4-amino-4-carboxychroman-2-one | cyanidol | luteolin-7-glucuronide | rosmarinic-acid |
| 4-arabinosyl-ellagic-acid | cysteine | luteolin-7-o-β-glucopyranoside | rosmariquinone |
| 4-hydroxy-tritriacontane-16,18-dione | daidzein | luteolin-7-o-β-glucoside | rosmarol |
| 4-ketopinoresinol | daidzin | lycopene | rubrobrassicin |
| 4-o-caffeoylquinic-acid | dehydrocurdione | m-hydroxybenzaldehyde | rutin |
| 4-terpineol | dehydroleucodine | machilin-d | s-allyl-cysteine-sulfoxide |
| 5,7-dihydroxycoumarin-7-methyl-ether | delphinidin | magnolol | s-allyl-l-cysteine |
| 5,8-dihydroxy-benzopyranone | delphinidin-3-glucoside | mahanimbine | s-allylmercaptocysteine |
| 5-hydroxy-8-o-beta-d-glucopyranosyl-benzopyranone | delphinidin-3-o-β-d-galactoside | mahanine | s-methylmercaptocysteine |

TABLE I-continued

| | | | |
|---|---|---|---|
| 5-o-beta-d-glucopyranosyl-3-1-(4-phenyl)-decane | delphinidin-3-o-β-d-glucoside | mahimbicine | salicylic-acid |
| 5-o-caffeoylquinic-acid | delphinidin-chloride | malonyldaidzin | salvianolic-acid-a |
| 6''-o-acetyl-daidzin | delta-5-avenasterol | malonylgenistin | salvianolic-acid-b |
| 6''-o-acetyl-genistin | delta-7-avenasterol | maltol | sanguinarine |
| 6,7,4'-trihydroxyisoflavan | delta-tocopherol | malvidin | saururin-a |
| 6,7,4'-trihydroxyisoflavanone | delta-tocotrienol | malvidin-3-garactoside | schizandrin |
| 6,7,4'-trihydroxyisoflavone | demethyltexasin | malvidin-3-o-α-l-galactoside | sciadopitysin |
| 6,7-di-4'-methoxyisoflavan | diallyl-disulfide | malvin | scopoletin |
| 6,7-di-4'-methoxyisoflavanone | diallyl-heptasulfide | mangiferin | scutellarein |
| 6,7-di-4'-methoxyisoflavone | diallyl-hexasulfide | mannitol | scutellarein-7-o-glucuronide |
| 6,7-dihydroxy-4'-methoxyisoflavan | diallyl-pentasulfide | martynoside | secoisolariciresinol |
| 6,7-dihydroxy-4'-methoxyisoflavanone | diallyl-sulfide | maytenolide | selenium |
| 6,7-dihydroxy-4'-methoxyisoflavone | diallyl-tetrasulfide | melatonin | sesamin |
| 6,7-dihydroxycoumarin | diallyl-trisulfide | methionine | sesaminol |
| 6-gingerdiol | dicaffeoylquinic-acid | methyl-3,4-dihydroxy-benzoate | sesaminol-gossypol |
| 6-gingerol | dihydroauercetin | methyl-caffeate | sesamol |
| 6-shogaol | dimethyl-sulfoxide | methyl-carnosate | sesamolin |
| 7,8-dihydroxyflavone | dioscorin | methyl-eugenol | sesamolinol |
| 7-n-butoxy-3,2',5'-trihydroxyflavone | dl-cysteine | methyl-gallate | shikimic-acid |
| 7-[3-(3,4-dihydroxy-4-hydroxymethyl-tetrahydro-furan-2-yloxy)-4,5-dihydroxy-6-hydroxy-methyl-tetrahydro-pyran-2-yloxy] | dodecyl-gallate | methyl-p-hydroxybenzoate | silibinin |
| acanthoic-acid; acetoxy-pinoresinol | eleutheroccal | methylhydroquinone | silybin |
| acetyl-eugenol | ellagic-acid | morelloflavone | silymarin |
| acetylcurcumin | ellagitannin | morin | sinapic-acid |
| aescin | embelin | myrcene | sparteine |
| Aesculin | epicatechin | myricetin | spermidine |
| alanine | epicatechin-3-o-gallate | myricetin-3-o-α-l-arabinopyranoside | spermine |
| alantolactone | epicatechin-gallate | myricitrin | spiraeoside |
| Alizarin | epigallocatechin | myrigalone-b | squalene |
| allantoin | epigallocatechin-3-o-gallate | myristic-acid | stigmasterol |
| Allicin | epirosmanal | myristicin | strychnine |
| Alliin | eriodictyol | myristoleic-acid | sucrose |
| Allixin | escin | n,n'-[2,2'-(5,5'-dihydroxy-4,4'-bi-1h-indol-3,3'-yl)-diethyl]-di-p-coumaramide | sulforaphane |
| allyl-mercaptan | esculin | n,n'-[2,2'-(5,5'-dihydroxy-4,4'-bi-1h-indol-3,3'-yl)-diethyl]-diferulamide | superoxide-dismutase |
| α-boswellic-acid | ethyl-β-d-glucopyranosyl-tuberonate | n-acetylcysteine | syriacusin-a |
| amentoflavone | ethyl-gallate | n-α-(1-deoxy-d-fructos-1-yl-)-l-arginine | syriacusin-b |
| ampelopsin | euchrestine-b | n-cis-ferulolytyramine | syriacusin-c |
| andrographolide | eugenol | n-fructosyl-arginine | syringaldehyde |
| andrographoside | eupatriol | n-fructosyl-glutamate | syringic-acid |
| anethole | ferulic-acid | n-p-coumaroyl-serotonin | tamarixetin |
| Anisole | feruloylhistamine | n-trans-ferulolytyramine | tangeretin |
| apigenin | fisetin | n-tritriacontane-16,18-dione | tannic-acid |
| apocynin | forsythoside-b | n-tritriacontane-18,18-dione | tannin |
| apomorphine | fraxin | n-[2-(5-(β-d-glucosyloxy)-1h-indol-3-yl)-ethyl]-ferulamide | taurine |
| arenarioside | fucoxanthin | n-[2-(5-(β-d-glucosyloxy)-1h-indol-3-yl)-ethyl]-p-coumaramide | taxifolin |

TABLE I-continued

| | | | |
|---|---|---|---|
| ascorbic-acid | fumaric-acid | naringenin | tellimagrandin |
| ascorbyl-palmitate | furaneol | naringin | terpinen-4-ol |
| aspalathin | galangin | nasunin | tetragalloylguinic-acid |
| atractylon | gallic-acid | neoandrographolide | tetrahydrocurcumin |
| Aucubin | gallic-acid-4-o-β-d-glucopyranoside | neohesperidin | tetrandrine |
| bacoside-a | gamma-oryzanol | norbixin | tetrasulfide |
| Baicalin | gamma-terpinene | nordihydroguaiaretic-acid | theaflavin |
| ballotetroside | gamma-tocopherol | norisoguaiacin | thearubigen |
| berbamine | gamma-tocotrienol | nothofagin | thioctic-acid |
| β-amyrin-acetate | garcinol | octyl-gallate | thonningianin-a |
| β-carotene | gardenoside | oleanolic-acid | thonningianin-b |
| β-d-tagatose | geniposide | oleuropein | thrachrysone |
| β-sitosterol | geniposidic-acid | opc | thymol |
| betanidin | genistein | opcs | thymoquinone |
| Betanin | genistin | orientin | tocopherol |
| bilobalide | gentisic-acid | osagin | trans-anethole |
| bilobetin | geraniin | otobain | trans-ferulic-acid |
| bis-demethoxycurcumin | gingerol | oxyacanthine | trans-p-menth-8-en-7-yl-caffeate |
| bisepoxylignan | ginkgetin | oxyresveratrol | triallylsulfide |
| bismurrayafoline-e | ginkgolide | p-coumaric-acid | tricin |
| Bixin | ginkgolide-a | p-cymene-2,3-diol | tridecanoic-acid |
| Boldine | ginkgolide-b | p-cymene-2,3-diol-6,6'-dimer | trimethylamine |
| boswellic-acid | ginkgolide-c | p-hydroxy-benzoic-acid | tryptophan |
| brevifolin | ginkgolide-j | p-hydroxycinnamic-acid | turmerin |
| broussoaurone-a | ginkgolides | palmitic-acid | turmeronol-a |
| broussochalcone-a | glutathione | pedunculagin | turmeronol-b |
| broussoflavan-a | glycitein | pelargonidin | tyrosol |
| broussoflavonol-f | glycitein-7-0-glucoside | penta-o-galloyl-β-d-glucose | ubiquinol |
| broussoflavonol-g | glycyrrhetic-acid | pentadecanoic-acid | ubiquinone |
| Brucine | glycyrrhetinic-acid | pentasulfide | ubiquinone-g10 |
| buplueran-2iic | glycyrrhizin | peonidin-3-(caffeoyl-sophoroside)-5-glucoside | ursolic-acid |
| Butein | gossypetin | peonidin-3-o-β-d-glucoside | uvaol |
| caffeic-acid | gossypin | persenone-a | vanillic-acid |
| Caffeine | gossypol | persenone-b | vanillic-acid-β-glucoside |
| caffeoyl-l-malic-acid | hamamelitannin | petunidin-3-o-β-d-galactoside | vanillin |
| campesterol | heptadecanoic-acid | petunidin-3-o-β-d-glucoside | verbascoside |
| campesteryl-ferulate | heptasulfide | phenol | verbascosides |
| camphene | hesperidin | phenyl-glucoside | vicenin |
| capsaicin | hesperitin | phlorotannin | vinyl-caffeate |
| capsaicinol | heterodendrin | phylligenin | virolin |
| capsanthin | hexasulfide | phytic-acid | vitamin-e |
| carnosic-acid | hibiscuside | piceatannol | vitexin |
| carnosol | hispidulin | piceid | wedelic-acid |
| carnosolic-acid | histidine | pinoresinol | wogonin |
| carvacrol | honokiol | piperine | polyphenols |
| Catalase | humulone | plumbagin | pomiferin |
| Catechin | hydroquinone | polydatin | proanthocyanidins |

Anti-Glycation Agent

An additional agent that may be added to the lipoic acid, carnosine, and carnitine formulation of the present invention is an anti-glycation agent. As used herein, the term "anti-glycation agent" means a compound for preventing and/or reducing the glycation of skin proteins, in particular of dermal proteins such as collagen. The anti-glycation agent will inhibit the formation of advanced glycation end products (AGEs).

Examples of anti-glycation agents are plant extracts of the Ericaceae family, such as an extract of blueberry (*Vaccinium angustifolium*); ergothioneine and its derivatives; and hydroxystilbenes and their derivatives, such as resveratrol and 3,3',5,5'-tetra-hydroxystilbene. Other exemplary inhibitors of AGE formation include, but are not limited to benfo-tiamine, pyridoxamine, G-rutin (Nagasawa T., *Mol Cell Biochem.* 249(1-2):3-10, 2003); pyridoxal phosphate, aminoguanidine, a aminoguanidine-pyridoxal adduct, green tea (Ouyang P. *Di Yi Jun Yi Da Xue Xue Bao* 24(3): 247-51, 2004); extracts of *Thymus vulgaris* (Morimitsu et al., *Biosci Biotechnol Biochem* 59(11):2018-21, 1995); Ge-132(2-carboxyethyl germanium sequioxide) (Unakar et al., *Exp. Eye Res.* 61(2): 155-64, 1995); curcumine (Sajithlal et al., *Biochem Pharmacol.* 56(12):1607-14, 1998); extracts of *Cratoxylum cochinchinense* (Tang, S Y et al., *Free Radic. Biol. Med.* 36(12):1575-87, 2004); extracts of *Apocynum venetum* Luobuma (Yokozawa et al., *Food Chem. Toxicol.* 42(6):975-81, 2004); carnosinylated proteins (Hipkiss A R et al., *Cell Mol Life Sci.* 57(5):747-53, 2000); extracts of *Eisenia bicyclis* (Okada et al., *Nat. Prod.* 67(1):103-5, 2004); rutin (Kiho, T et al., *Biosci. Biotechnol. Biochem.* 68(1):200-5, 2004); amadoriase enzymes from *Aspergillus* fungi (Monnier V M et al., *Biochem. Soc. Trans* 31:1349-53, 2003; U.S. Pat. No. 6,605, 642), guanidine rich extracts of *Galega officinalis*, and extracts of *lycopersicon esculentum*. The AGE inhibitor as described herein may be incorporated in amounts from about 0.001%-30% by weight. More preferably, the AGE inhibitor is incorporated in amounts from about 0.1%-5% by weight, based of the total weight of the preparation.

An anti-glycation agent of interest is garcinol. Garcinol occurs naturally in the latex exudate of the herb *Garcinia Cambogia*, which is used as a weight loss supplement. Garcinol is a moderate antioxidant, metal chelators, and free radical scavenger. It also is a superoxide anion scavenger and has been shown to suppress glycation in a bovine serum albumin/fructose system. (Yamaguchi F. et al., *J Agric Food Chem.* 2000 February; 48(2):180-5) It has also been shown that the (−)-hydroxycitrate from *Garcinia* fruits may aid endurance during post-absorptive aerobic exercise by promoting gluconeogenesis. *Garcinia* is particularly useful as an additional agent because the combination of garcinol with carnitine and chromium (i.e., as part of a chelated with carnosine) will have anti-glycation and promote gluconeogenesis (McCarty MF. *Med Hypotheses.* 1995 September; 45(3): 247-54).

Aglycal LS 8777, made by Laboratoires Serobiologique (Cognis France), may also be included as an anti-glycation agent in the formulation of the present invention. Aglycal LS 8777 is a plant-based complex that retards the glycation of proteins. This photo-complex aids in the long-term elasticity of the skin and protect against the fragmentation of collagen. (www.laboratoires-serobiologiques.com)

Aldenine, made by Lipotec (Spain) is a complex of a tripeptide and hydrolyzed wheat and soy proteins that boosts Collagen III synthesis while protecting cells from photo damage. Aldenine detoxifies the skin from harmful RCS (Reactive Carbonyl Species).

Another anti-glycation agent, Antiglyskin® from Silab is rich in phenolic acids and glycopeptides from sunflower and inhibits the protein glycation reaction and prevents the glyco-oxidation.

Compounds obtained from *Pterocarpus marsupium* may also be incorporated into the topical formulation. (−) Epicatechin, the active ingredient in the Indian herb *Pterocarpus marsupium* Roxb, can be obtained from the water extract of the bark and is insulinogenic. (Ahmad F, et al., *Acta Diabetol Lat.* 1989 October-December; 26(4):291-300). It has been found to decrease hepatic and skeletal muscle glycogen (Grover J K, et al., *Mol Cell Biochem.* 2002 December; 241 (1-2):53-9). In addition, three flavonoid antioxidants are also present in the heartwood; these flavonoid are marsupsin, pterosupin, and liquiritigenin. The gum tannic acid and a non-glucosidal tannin, kino tannic acid. *Pterocarpus marsupium* extracts have also been shown to have anti-oxidant activity Katiyar S K, et al., *Photochem Photobiol.* 1995 November; 62(5):855-61) and a strong anti-glycation agent (www.laboratoires-serobiologiques.com/LSvi/english/prod_2.html).

N-Acetylcysteine is an N-acetylated cysteine which is a thiol containing amino acid, also called α-acetamido-β-mercaptopropanoic acid, which is a preferred additional component of the present invention. The incorporation of N-acetylcysteine into the topical formulation will improve the signs of aging of the skin. N— acetylcysteine is an antioxidant and also has been indicated as protective against pulmonary oxygen toxicity (*Eur. Respir. J.* 2: 116-126 (1989)). It is also an anti-glycation agent. Preferred forms of N-acetyl cysteine include: N-acetyl-L-cysteine, N-acetyl-L-cysteine amide, N-acetyl-L-cysteine methyl ester, N-acetyl-L-cysteine ethyl ester, N-acetyl-L-cysteine propyl ester, and N-acetyl-L-cysteine isopropyl ester. See PCT US96/16534, teaching topical compositions containing N-acetylcysteine and U.S. App. 20030229141 which discloses the topical use of N-acetyl cysteine to alleviate or improve various cosmetic conditions and dermatological disorders.

One preferred AGE inhibitor is benfotiamine. The term benfotiamine also encompasses benfotiamine derivatives such as S-Benzoylthiamine O-monophosphate. Benfotiamine is the most potent of the allithiamines, an unique class of thiamine-derived compounds present in trace quantities in roasted crushed garlic and other vegetables from the *Allium* genus (such as onions, shallots, and leeks). Benfotiamine's unique open-ringed structure makes it able to pass directly through cell membranes, readily crossing the intestinal wall and being taken straight into the cell, and is absorbed by the body better than thiamine itself, and levels of thiamine and thiamine pyrophosphate remain higher for longer, thereby decreasing the formation of AGEs.

Another preferred AGE inhibitor is pyridoxamine. Pyridoxamine (4-aminomethyl-5-hydroxy-6-methyl-3-pyridinemethanol) and derivatives of pyridoxamine such as 4-aminomethyl-5-hydroxy-6-methyl-3-pyridinemethanol dihydrochloride and 4-aminomethyl-5-hydroxy-6-methyl-3-pyridylmethyl phosphate may be incorporated in the lipoic acid, carnosine and carnitine formulation of the present invention. Pyridoxamine, is a vitamin B6 derivative, which is water-soluble and nontoxic in rats and humans. It inhibits the formation of AGEs from Amadori proteins and is classified as a post-Amadori inhibitor (Khalifah et al. *Biochem. Biophys. Res. Comm.* 199:257, p. 251-258). It is also believed that pyridoxamine traps reactive dicarbonyl intermediates in AGE formation and may also decrease oxidative stress which subsequently decreases AGE formation from reactive oxygen species (Iacovella et al. *SCJMM,* 2004: 5, p. 73-101). Pyridoxamine has also been shown to inhibit advanced lipoxidation end products (ALES) (Onorato J M. et al., *J. Biol. Chem.* 275(28):21177-84 (2000)). Decreasing ALEs formation is accomplished by decreasing the concentration of an oxidiable substrate such as glucose and blood lipids. (Metz T O, et al., *Arch Biochem Biophys.* 419(1):41-9 (2003)). It has been proposed that the antioxidant properties of pyridoxamine be used for the inhibition of ALE as well as AGE formation and development of complications of diabetes and hyperlipidemia (Mene P, et al., *Am J Cardiovasc Drugs.* 3(5):315-20 (2003)). U.S. Pat. Nos. 6,750,209 and 6,740,668 demonstrate the difference in pyridoxamine and the other B6 vitamins as inhibitors of post-Amadori antigenic AGE formation. The efficacy of inhibition of overall glycation of protein, in the presence of high concentrations of sugar, was not predictive of the ability to inhibit the post-Amadori steps of AGE formation where free sugar is removed. Pyridoxamine has been shown to be the strongest AGE inhibitor of the B vitamins. (Price, D. L., *J. Biol. Chem.* 2001 December 28; 276(52): 48967-72).

The AGE inhibitor that may be added to the formulation includes two types of enzymes, fructosyl lysine oxidase and fructose lysine 3-phosphokinase, which catalyze the deglycation reaction and generate free amine groups. The biochemical properties of these amadoriase enzymes and their role in protein deglycation are described by Wu, X et al., *Arch Biochem Biophys.* 419(1):16-24 (2003). See also Takahasi, M. et al., *J. Biol. Chem.* 272, 3437-43 (1997). The amadoriase enzymes are particularly useful since they have strong antiglycation activity, and some of these compounds are selective for collagen.

Another class of AGE inhibitors that may be used in the formulation of the present invention are described by Rahbar et al., *Molecular Cell Biology Research Commun.* 3, 360-66 (2000). These compounds are benzoic acid derivatives, aryl and heterocyclic ureido compounds, and aryl and heterocyclic carboxamido phenoxy isobutyric acids. They have been shown to be potent inhibitors of glycation, and have been shown to inhibit the glycation of collagen. The compounds described by Wu, Takahasi, or Rahbar may be used in combination with formulation described herein. In a preferred embodiment, this combination also includes carnosine.

Other AGE inhibitors that may be added to the formulation of the present invention. Extracts of *Paeonia suffruticosa* have been shown to be AGE inhibitors (Qkano et al., at www.creative-developments.co.uk/papers/Natural %20Ingredients %-201998.html). Additionally, AGE inhibitors have been isolated along with compounds having antioxidant activity from *Paeonia suffruticosa*; these compounds include the monoterpene glycoside, α-benzoyloxypaeoniflorin, β-benzoyloxypaeoniflorin, paeonolide, paeoniflorin and mudanpioside H. (Ryu G., et al, *Arch Pharm Res.* 2001 April; 24(2):105-8). Another AGE inhibitor is from extracts of *Sanguisorba officinalis*, which has been shown to reduce chronic photodamage to the skin. (Tsukahara K., Biol *Pharm Bull.* 2001 September; 24(9):998-1003). *Pterocarpus marsupium* has been shown to be an anti-diabetic agent and strong antihyperglycaemic agent (Babu P S., *J. Pharm Pharmacol.* 2004 November; 56(11):1435-42). *C. Cochinchinense* has been found to be a particularly potent AGE inhibitor on proteins and also strongly inhibited hypochlorous acid-induced DNA damage. (Tang S Y, *Free Radic Biol Med.* 2004 Jun. 15; 36(12):1575-87).

There are other natural products that are AGE inhibitors, which may be used in the present invention. The screening method described by Matsuura, based on a fluorometric analysis, may be used to determine the inhibitory index of the Maillard reaction and AGE inhibition to determine compounds useful to include in the formulation of the present invention. (Nobuyasu Matsuura et al. *J. Health Science* 48(6) 520-526 (2002)).

Collagen Enhancing Agents

Collagen enhancing agents such as those described herein may also be added to the present formulation. Agents having 'Collagenic activities' include the anthocyanidins, ascorbic acid, asiatic acid (such as from centella asiatica), aucubin, proanthocyanidins, stabilized vitamin C, the amino acids 1-lysine, 1-proline and their derivatives (e.g., dipalmitoyl-hydroxy-proline, hydroxyproline, homoproline, and natural raw materials containing these such as apt (*Ahnfeltia concinna*) available from CIR),), and copper peptides. Agents having 'Collagenase-Inhibitor activities' include the anthocyanidins, eicosapentaenoic acid, proanthocyanidins, procyanidins, bovine cartilage extracts and glycosaminoglycans from shark. Agents having 'Collagen-Sparing activities' include caffeic acid, chlorogenic acid, cichoric acid, cynarin, and echinacoside. Each of these may be used in addition to the lipoic acid, carnitine, and carnosine of the present invention. Alternatively, collagen itself may be added to the formulation such as in the form of collagen peptides (e.g. Active Collagen Polypeptide available from Shanghai UChem Co. LTD.) or in a form adapted for delivery to the skin so that the collagen will penetrate into the skin (e.g., the form described in U.S. Pat. No. 6,759,056).

Additional collagen inducing agents are growth factors, such as EGF, FGF, TGF, TGF-β, HGH (offered in a nanoliposome encapsulation by Regernon, Inc)., NGF, KGF, IGF, natural sources containing growth factors such as colostrums (Pepha® Nutrix from Centerchem), deer antler preparations and peptides designed to increase the production of any of these growth factors (e.g., Syn®-col from Centerchem-TGF-β, Hericium Erinaceus and Idebenone-NGF) or the production of collagen itself (e.g, Matrixyl300, Dermaxyl, and Calmosensine each from Sederma), and collagen peptides. Glucosamine, glucoseamine sulfate, glucosamine HCl, glucosamine ascorbate, chondroitin sulfate and other glucosamine salts and derivatives may be used in the formulation to induce collagen. Manganese gluconate, a common source of manganese, may also be included in the formulation. The enzyme MnSOD is a powerful antioxidant that removes superoxide radicals.

In one embodiment, a silicon, or an ortho silicic acid described in U.S. Pat. No. 5,922,360 may be used. This ingredient may be used to boost collagen production.

Mitochondrial Resuscitants

Mitochondrial resuscitants (in addition to the lipoic acid and carnitine) may also be added to the lipoic acid, carnosine, and carnitine formulation. Mitochondrial decay in aging is a major driving force behind the aging process. (*Ann N Y Acad Sci.* 2004 June; 1019:406-11; *Proc Natl Acad Sci USA.* 1994 91:10771-8). The mitochondria are the powerhouses of the cell responsible for producing all cellular energy and convert carbohydrates and fatty acids into ATP. ATP is necessary for the production of proteins, which declines with aging (e.g., collagen and elastin).

In addition to carnitine and lipoic acid (Ames B., *Ann. N.Y. Acad. Sci.* 1033: 108-116 (2004), agents useful as mitochondrial resuscitants include, but are not limited to N-tert-butyl hydroxylamine (NTBHA), COQ10, CoA, NADH, FADH, succinic acid, creatine, D-ribose, Sepitonic M3® (containing magnesium aspartate, zinc gluconate, copper gluconate), pyruvate, gymnostemma pentaphyllum, cytochrome C, idebenone, and particular SODs including manganese superoxide dismutase (Mn—SOD). Additionally, agents including phenylbutylnitrone (PBN) and other spintraps, such as the nitrone or nitroso spin traps described in U.S. Pat. No. 5,723,502 (N-t-butyl-α.-phenylnitrone, 3,5-dibromo-4-nitrosobenzenesulfonic acid, 5,5-dimethyl-1-pyrroline N-oxide, 2-methyl-2-nitrosopropane, nitrosodisulfonic acid, α.-(4-pyridyl-1-oxide)-N-t-butylnitrone, 3,3,5,5-tetramethylpyrroline N-oxide, and 2,4,6-tri-t-butylnitrosobenzene) may be used. These agents are antioxidants as well as mitochondrial resuscitants.

NTBHA is a particularly preferred mitochondrial resuscitant. NTBHA has great potential for maintaining mitochondrial health by helping to reduce or reverse mitochondrial damage and control aging at the cellular level. This powerful antioxidant has been shown to prevent the loss of mitochondrial enzyme glutamate dehydrogenase (gdh) and aconitase, a key kreb's cycle enzyme, and to be useful as an oral agent for treating diseases relating to oxidation damage. (U.S. Pat. No. 6,455,589). NTBHA protects mitochondria and proteins from oxidative damage and simultaneously reverses existing damage in the mitochondria. NTBHA can be used to simultaneously minimize oxidative stress and increase energy by enhancing atp production. This effect is similar to that shown to occur for the dietary supplementation using acetyl-1-carnitine to increase cellular respiration, mitochondrial membrane potential, and cardiolipin values where PBN was administered to lowered oxidant production to improve mitochondrial function without a significant increase in oxidative stress. (Hagen, T M et al., *Ann. NY Acad. Sci.* 1998; 854:214-23). Additionally, NTBHA is an antiglycating agent; this is beneficial for several reasons, including reducing the depth and/or numbers of wrinkles on the skin. Since glycation interferes with muscle function, the antiglycating activity of NTBHA could prevent or delay the loosening of the facial muscles underlying the sagging skin as the muscles age. Other n-hydroxylamines may also be incorporated in the formulation of the present invention. These include, for example, n-benzyl hydroxylamine and n-methyl hydroxylamine. (Atamna, H., et al., FASEB J. 2001 October; 15 (12):2196-204; Ames, B N et al., Sci. World J. 2001; 1: 81-82sr).

Manganese superoxide dismutase (MnSOD) is a mitochondrial enzyme that protects cells from oxidative damage. MnSOD works as an antioxidant to remove superoxide radicals. MnSOD is particularly useful when added to the formulation of the present invention since it may be used in reducing oxidative damage due to increased ATP concentrations caused by the topical agents o the present invention.

MnSOD mimetics such as atrium compounds may also be used as mitochondrial anti oxidants.

Thioredoxin

Thioredoxins are small proteins with a redox active disulfide bridge present in the characteristic active site sequence: -Trp-Cys-Gly-Pro-Cys- (tryptophane-cysteine-glycine-proline-cysteine). Thioredoxins have a molecular mass of approximately 12,000 and is reduced by NADPH and the enzyme NADP-thioredoxin reductase. Reduced thioredoxins are electron donors in a variety of cellular redox reactions and help control free radicals in tissues. U.S. Pat. Pub 20060008487 describes the use of thioredoxin for the treatment of skin damage. Thioredoxins are particularly useful in the formulations of the present invention since they reduce the free radicals found in the mitochondria.

D-ribose is a naturally occurring five-carbon sugar found in all living cells, and is another particularly preferred mitochondrial resuscitant. It is not an essential nutrient, since it can be made in the body from other substances, such as glucose. ATP (adenosine triphosphate) requires D-ribose, as does nucleotides, nucleotide coenzymes, and RNA (ribonucleic acid). D-ribose, in the form of ribonucleoside diphosphates, is converted to deoxyribonucleoside diphosphates, precursor molecules for DNA. D-ribose in RNA and D-deoxyribose in DNA. When D-ribose is added to the formulation, it is particularly preferred to additionally include an AGE inhibitor to prevent the potential glycating effect of d-ribose.

ATP, adenosine 5'-monophosphate (AMP), and their degradation products may also be administered directly as agents in the topical formulation of the present invention. U.S. Pat. No. 5,227,371 teaches the oral or topical administration of AMP, ATP or their degradation products adenosine and inorganic phosphate to increase ATP levels. Extracellular ATP has been shown to help regulate vascular tone (Burnstock, G. and Kennedy, C Circul. Res. 1986, 58, 319-330), promote muscle contractions (Burnstock, G. Pharmacol. Rev. 1972, 24, 509-581), and arresting tumor growth (U.S. Pat. No. 5,049,372). When ATP or other agents susceptible to degradation are used, a stabilized form of the agent is preferred.

Glutathione

Glutathione, reduced glutathione, glutathione peroxidase, glutathione s-transferase or glutathione reductase may be incorporated in the formulation of the present invention. Additionally, synergistic intracellular glutathione inducers and precursors of glutathione may be used. These include ornithine, α-ketoglutarate, 1-cystein, 1-glycine, 1-glutamatic acid, glycyl-1-glytamine, n-acetyl-cystein, riboflavin, vigtamin B6, parsley seed or seed extract, sylimarin, and cysteine whey peptides. Other ingredients synergistic with glutathione or glutathione precursors which may be added to the formulation include: selenium salts, amino acid chelates (including methyl-1-selenocysteine, 1-selenomethionine) and sacharomyces selenium ferment, polyenylphosphatidylcholine, myristicin (which may be isolated from parsley), dihydromyristicin, quercetin, riboflavin, purselane extract, spinach extract, N-acetyl-cysteine, n-acetyl-glutamine, n, ndimethylglycine, anthocyanins, pycnogenol (*pinus maritima*) extract, grape seed extract, turmeric extract, sylimarin, tocopherols, r-lipoic acid, *cynara scolymus* extract, *Picrorhiza kurrooa* extract, *Tinospora cordifolia* extract, *Phyllanthus niruri* extract, *Terminalia belerica* extract, *Terminalia chebula* extract, *Phyllanthus emblica* extract, *Boerhavia diffusa* extract, Defensine (available from Silab), *Phyllanthus amarus* extract, *Hibiscus rosa sinensis* extract, gentisic acid, *Tephrosia purpurea, Andrographis paniculata* extract, *Occinum santum* extract and cysteine peptides. Additionally, SUNACTYL® LS 9610 and AFR® LS 4467/VEG (from Laboratoires serobiologique) may be used.

Glutathione is a tripeptide consisting of the amino acids glutamic acid, cysteine, and glycine. Glutathione is important for the maintenance of the function of enzymes in cell metabolism. It assists in the transport of amino acids across cell membranes. It prevents oxidative alterations of catalytic and allosteric centers, and upholds the optimum conformation of the enzymes for proper functioning (see WO 89/00427). The formation of cataracts is also associated with decreased levels of glutathione. It has been suggested that NADPH production from D-glucose aids in glutathione regeneration and protection from mitochondrial dysfunction, and thereby providing a neuroprotective effect. (Delgado-Esteban M, et al., *J Neurochem.* 2000 October; 75(4):1618-24). U.S. Pat. No. 6,573,299 describes the addition of glutathione in a formulation containing a hydroxy acid. Glutathione has also been shown to be an ACE inhibitor (IC50=3.2 µg/ml), anticytotoxic, antieczemic, antihepatitic, a cancer-preventive, and useful treating heavy metal poisoning. In this formulation glutathione is particularly useful as it is involved with preventing both oxidative damage and detoxifying RCS (reactive carbonyl species). When skin is exposed to UVB endogenous is depleted and cannot perform its protective role. Therefore replenishing can be a crucial step towards preventing photoaging. Furthermore detoxify RCS such as 4-hydroxynonenal by forming adducts with. Therefore can be considered an antiglycation agent to work synergistically with carnosine in this formulation. Therefore, the combination of glutathione in a topical formulation is particularly useful.

Glutathione peroxidase catalyzes the reduction of hydroperoxides, such as hydrogen peroxides, by reduced glutathione and protects the cell from oxidative damage. Most glutathione peroxidase enzymes are tetramers having four identical subunits containing selenocysteine in the active site which participates directly in the two-electron reduction of the peroxide substrate. Glutathione is used as an electron donor to regenerate the reduced form of the selenocysteine. (Forstrom, J. W., et al., *Biochemistry* 17, 2639-2644 (1978); Paglia, D. E., Valentine, W. N. *J Lab Clin Med* 70, 158-169 (1967). Glutathione peroxidase can be added to a topical formulation to protect the skin for oxidative damage.

Glutathione also affects melanin in the skin. Melanin, or skin pigment, is produced by melanocytes. There are two common types of melanin in hair, eumelanin, which is brown/black in color, and phaeomelanin, which is red/yellow in color. Glutathione has been implicated in the biogenesis of the melanin precursor 5-S-cysteinyldopa and the melanogenic activity of pigment cells. Along with cysteine (which is used for glutathione biosynthesis), glutathione will effect the melanin and therefore coloration of the skin. (Benathan M. et al., *Cell Mol Biol* (Noisy-le-grand). 1999 November; 45(7): 981-90). Further, glutathione-reductase plays an important role in the regulation and control of the biosynthetic activity of melanocytes. The differences in the glutathione and the glutathione enzyme content in eumelanin and phaeomelanin pigmentation in skin indicates that the increase of glutathione reductase activity in the environment of the melanocytes may stimulate the pigment cells to produce phaeomelanin instead of eumelanin pigment. (Benedetto J P et al., *J Invest Dermatol.* 1982 December; 79(6):422-4). Skin with no active melanocytes shows glutathione levels intermediate between those of eumelanin and phaeomelanin. This is consistent with glutathione reductase activity playing an important role in the regulation and control of the biosynthetic activity of melanocytes. (Benedetto J P, et al., *Invest Dermatol.* 1981 November; 77(5):402-5). Glutathione also affects hyperpigmentation of the skin. Hyperpigmentation, caused by inflammatory skin disorders such as eczema, allergic contact dermatitis, and irritant contact dermatitis acne, is often treated using sunscreen and an agent such as a hydroquinone, tretinoin, azelaic acid, or kojic acid. (Pathak M A, Fitzpatrick T B, Nghiem P, Aghassi D S. Fitzpatrick T B, Editor. Dermatology in General Medicine, 4th ed, New York: McGraw-Hill, pp 2742-60 (1993). Glutathione plays a key role in the depigmenting and melanocytotoxic action these agents, which act to decrease intracellular glutathione by stimulating pheomelanin rather than eumelanin and thereby lightening hyperpigmentation of the skin. (Alena F, et al., *Invest Dermatol* 104(5):792-7 (1995)). Therefore, the use of the topical composition of the current invention can be used to treat hyperpigmentation as well as affect the signs of aging.

Centrophenoxine (Lucidril®) is another agent that may be added to the formulation of the present invention. It contains both dimethylaminoethanol (DMAE) and p-chlorophenoxy-acetate. DMAE is found in food and is also a metabolite. pCPA is a synthetic compound related to plant hormones known as auxins. Centrophenoxine has been shown to remove lipofuscin, a cellular residue that accumulates over the life of the cell. Additionally, it has been shown to have an effect as a cognition enhancer. (J. Am. Geriatr. Soc. (USA), 1978, 26:2, 74-81.)

NADH

Nicotinamide-adenine-dinucleotide (NADH), in its reduced form, is a coenzyme form of vitamin B3 (niacinamide) which occur in all living cells including human cells. Similarly nicotinamide-adenine-phosphate-dinucleotide (NADPH) is the phosphoralated form of NADH, and as used herein, NADPH is included in the term "NADH." NADH may be added to the formulations of the present invention.

NADH stimulates the production of ATP (adenosine triphosphate) during the regulation and release of stored energy. Higher levels of NADH in the cell allow for the release of energy. Because of this, the oral administration has been used to NADH treat fatigue, chronic fatigue syndrome, and fibromyalgia. There is also an indication that NADH may be useful in treating Alzheimer's disease (U.S. Pat. No. 5,444,053) treating Parkinson's disease (U.S. Pat. Nos. 4,970,200 and 5,019,561), depression, improving memory and concentration, and endurance.

The topical administration of NADH is described in U.S. Pat. No. 5,952,312, which demonstrates that NADH is adsorbed by the skin and stimulates enzymes essential in the production of energy. When NADH is included in the topical formulation, an additional stabilizer which inhibits oxidation of NADH may also be added. The stabilizer is $NaHCO_3$, ascorbic acid, sodium ascorbate, tocopherols, tocopherol acetate, polyvinylpyrolidone, or a combination thereof (U.S. Pat. No. 5,952,312).

The addition of NADH is useful in the formulation of the present invention because it allows for the conversion of R-lipoic acid into the more active DHLA. As DHLA works to remove the signs of aging in the skin, it is oxidized to the less effective R-lipoic acid. NADH will then reduce the lipoic acid to form DHLA, which then continues to remove the signs of aging. In compositions comprising DHLA, a carnitine and a carnosine, the addition of NADH is also useful because DHLA will be converted to lipoic acid upon contact with an oxidizing species in the skin; the NADH then effectively converts the lipoic acid back to DHLA.

Preferred compositions of NADH (or NADPH) in the topical formulation are 0.1%-10%, or more preferably 1%-5%.

Anti-Inflammatory Agents

The free radicals associated with aging skin will often also induce inflammation in the skin and lack of skin immunity. Therefore anti-inflammatory agents including NSAIDS, COX-2 inhibitors (e.g., nexrutine, ursolic acid, quercetin, curcumine, and evodia extract. (Kang, S. S., et al., Nat. Prod. Sci., 1999, 5(2): 65-69.) can be included in the formulation of the present invention.

Additional anti-inflammatory agents useful in combination with the lipoic acid, carnosine, and carnitine formulation are listed in Table II.

TABLE II

| | | | |
|---|---|---|---|
| (+)-alpha-viniferin | β-himachaline | forskolin | nepetrin |
| (+)-catechin | β-pinene | fraxin | nesodine |
| (+)-eudesma-4(14),7(11)-diene-3-one | β-santalene | friedelan-3-beta-ol | nevadensin |
| (+)-hernandezine | β-sitosterol | friedelin | niacinamide |
| (+)-pseudoephedrine | betonicine | fumoficinalne | nimbidin |
| (−)-16,17-dihydroxy-16beta-kauran-19-oic | betulin | galangin | nordihydroguaiaretic-acid |
| (−)-alpha-bisabolol | betulinic-acid | gallic-acid | oleanolic-acid |
| (−)-betonicine | bis-(4-hydroxy-cinnamoyl)-methane | gallocatechin-(4alpha->8)-epigallocatechin | oleic-acid |
| (−)-bornyl-caffeate | bis-desmethoxycurcumin | gallocatechin-(4alpha->8)-gallocatechin | olivetol |
| (−)-bornyl-ferulate | bisaboloxide | gallocatechin-(4alpha->8)-gallocatechin-(4alpha->8)-gallocatechin | omega-3-fatty-acids |
| (−)-bornyl-p-coumarate | boehmerol-acetate | gamma-boswellic-acid | opc |
| (−)-epicatechin | boldine | gaultherin | opcs |
| (1's)-1'-acetoxychavicol-acetate | borjatriol | genistein | orientin |
| (e)-4-(3',4'-dimethoxyphenyl)-but-3-en-ol | borneol | gentianaine | osthol |

TABLE II-continued

| | | | |
|---|---|---|---|
| 1,7-bis-(4-hydroxyphenyl)-1,4,6-heptatrien-3-one | boswellic-acid | gentianamine | paeoniflorin |
| 1,8-cineole | bowdichione | gentianidine | paeonol |
| 10-acetoxy-8-hydroxy-9-isobutyloxy-6-methoxythymol | bradykininase | gentianine | palmatine |
| 10-dehydrogingerdione | brazilin | gentiopicroside | palmidrol |
| 10-gingerdione | bromelain | gentisic-acid | palustroside |
| 13',ii8-biapigenin | broussochalcone-a | germacrone | papain |
| 13-oxyingenol-ester | bryonolic-acid | gingerol | parthenolide |
| 16,17-dihydroxy-16beta-kauran-19-oic | bupleurin | ginkgetin | pentagalloyl-glucose |
| 16-hydroxyingenol-ester | butein | ginkgolide | petiline |
| 2''-o-glycosylvitexin | butylidene-phthalide | ginkgolides | pheophytin-a |
| 2-beta,3beta-27-trihydroxyolean-12-ene-23,28-dicarboxylic-acid | cafestol | ginsenoside-r-o | pheophytin-b |
| 20-deoxyingenol-ester | caffeic-acid | gitogenin | phytolaccoside |
| 22beta-escin | caffeoylmaric-acid | glucosamine-sulfate | piperine |
| 24-methylene-cycloartanol | caffeoyltartaric-acid | glycyrrhetic-acid | platycodin |
| 3,4-secotriterpene-acid-20-epi-koetjapic-acid | calophyllin-b | glycyrrhetinic-acid | plumieride |
| 3-acetylaconitine | calophyllolide | glycyrrhizic-acid | podoverine-a |
| 3-beta-hydroxy-2,3-dihydrowithanolide-f | cannabichromene | glycyrrhizin | polygonolide |
| 3-n-butyl-phthalide | cannabidiol | gnaphaliin | procyanidin-a-2 |
| 3-o-acetyloleanolic-acid | cannabigerol | gossypin | propyl-gallate |
| 3-oxo-11-alpha-hydroxyolean-12-ene-30-oic-acid | cannflavin | guaiazulene | prostratin |
| 3-oxo-11-alpha-methoxyolean-12-ene-30-oic-acid | canniprene | haemocorin | protocatechuic-acid |
| 3-oxo-olean-9(11),12-diene-30-oic-acid | capsaicin | hanfangchin | protopine |
| 4-vinyl-guaiacol | carbenoxolone | harpagide | pseudoephedrine |
| 5-deoxyingenol-ester | carboxyatractyloside | harpagoside | punarnavine |
| 6,7-dimethylaesculetin | carnosine | hastatoside | quercetin |
| 6,7-dimethylesculetin | carnosol | hederagenin | quercetin-3-methyl-ether |
| 6-dehydrogingerdione | carvacrol | helenalin | quercetin-3-o-beta-d-glucoside |
| 6-deoxyjacareubin | caryophyllene | helenalin-esters | quercetin-3-o-beta-d-glucuronide |
| 6-gingerdione | caryophyllene-oxide | helliccoside | quercetin-3-o-galactoside |
| 6-o-(2''-acetyl-3'',4''-o-di-p-methoxy-cinnamoyl-α-1-rhamno-pyranosyl)-catalpol | catechin | heraclenin | quercetin-3-o-methyl-ether |
| 6-o-(4''-acetyl-2'',3''-o-di-p-methoxy-cinnamoyl-α-l-rhamno-pyranosyl)-catalpol | cepharamine | hernandezine | quercetin-3-rhamnoglucoside |
| 7-methoxycoumarin | cepharanoline | hesperidin | quercetin-pentamethyl-ether |
| 8-acetylharpagide | cepharanthine | holaphylline | quercitrin |
| 8-o-cinnamoylharpagide | chaksine | homoaromoline | quinovic-acid |
| Abrine | chamazulene | homocarnosine | quinovic-acid-gylcoside |
| acanthoic-acid | chelerythrine | humulone | resiniferatoxin |
| acetyl-11-keto-beta-boswellic-acid | chikusetsusaponin | hypaconitine | resveratrol |
| acetyl-beta-boswellic-acid | chikusetsusaponin-v | hyperin | ricinoleic-acid |
| acetylsalicylic-acid | chlorogenic-acid | hyperoside | rosmarinic-acid |
| acetylshikonin | chlorogenin | hypolaetin-8-glucoside | ruscogenin |
| aconitine | chrysanthemol | imperatorin | rutin |
| actinidoles | chrysin-5,7-dihydroxyflavone | inophyllolide | s-adenosylmethionine |
| Aescin | chrysosplenin | inosine | sabianine |
| aesculetin | chrysosplenol | isoalantolactone | saikosaponin |
| aesculin | chymotrypsin | isoelaeocarpine | saikosaponin-a |
| Ajoene | cinnamaldehyde | isoeugenol | saikosaponin-d |
| alantolactone | cinnamic-acid | isoferulic-acid | salicin |
| alkannin | cirsilineol | isoliquiritin | salicyl-salicylic-acid |
| allantoin | cis-communic-acid | isopimpinellin | salicylamide |
| Allicin | cis-spiroether | isoplumbagin | salicylates |

TABLE II-continued

| | | | |
|---|---|---|---|
| α-amyrin | clitoriacetal | isoquercitroside | salicylic-acid |
| α-amyrin-acetate | cnicin | isorhamnetin | saligenin |
| α-amyrin-palmitate | cnidilide | isotetrandrine | sanguinarine |
| α-bisabolol | colchicine | isothymonin | santamarin |
| α-boswellic-acid | colchicoside | isotrilobine | santamarine |
| α-curcumene | coniferyl-aldehyde | jaceidin | scandenolide |
| α-linolenic-acid | copper | jaligonic-acid | sciadopitysin |
| α-peroxyachifolide | copper-salicylate | jateorrhizine | scoparone |
| α-pinene | coptisine | jatrorrhizine | scopolamine |
| α-spinasterol | corilagin | kaempferide | scopoletin |
| amentoflavone | coumarin | kaempferitrin | sheganshu-a |
| amygdalin | crotaloburine | kaempferol | shikonin |
| andrographolide | cryogenine | kaempferol-4'-o-methylether | shogaol |
| anethole | cryptoaescin | kaempferol-7-glucoside | sideritoflavone |
| annomontine | cucurbitacin-b | kampferol-7-glucoside | silymarin |
| anthocyanoside | cuparene | kawain | sinapaldehyde |
| anthranilic-acid | curcumin | koparin | sinoacutine |
| apigenin | curcuminoids | 1-ephedrine | sinomenine |
| apigenin-7-glycoside | cycleanine | 1-glutathione | solasodine |
| apigenin-7-o-glucoside | cycloartenol | 1-pulegone | sparteine |
| apigenin-dimethyl-ether | cyclobuxine-d | lanceolarin | spinosin |
| apocynin | cyclosadol | lapachol | stigmasterol |
| ar-turmerone | cytisine | lawsaritol | superoxide-dismutase |
| arborinine | daidzein | lawsone | syringaldehyde |
| aristolochic-acid | damasceine | leiocarposide | tanshinone |
| artabsin | dauricine | leucoanthocyanidins | taraxasterol |
| artecanin | dehydrocycloguanandin | leucodelphinidin | taraxasterol-acetate |
| artemetin | delta-3-carene | licochalcone-a | taspine |
| arvenoside-a | demethoxycurcumin | licurizid | taxifolin |
| ascorbic-acid | demethyltetrandrine | lindleyin | tectoridin |
| asiaticoside | desmethoxyangonin | linoleic-acid | tectorigenin |
| asperuloside | dihydrohelenalin | liquiritic-acid | ternoside |
| Aspirin | dihydrohelenalin-esters | liquiritigenin | tetrahydrocurcumin |
| aspirin (acetylsalicylic-acid; not natural) | dihydrokawain | liquiritin | tetrandrine |
| astramembranin-i | dihydromethysticin | liquiritone | thalcimene |
| astringenin | diosgenin | loganin | thalfoetidine |
| atractylenolide | diosmin | lupeol | thalicsimine |
| atractylenolide-i | edpetiline | lupinine | thalmine |
| atractylenolide-ii | eicosapentaenoic-acid | luteolin | thalsimine |
| atractylenolide-iii | elaeocarpine | luteolin-7-glucoside | thymol |
| atractylochromene | elaidic-acid | madecassoside | tocopherol |
| atractylon | ellagic-acid | magnesium | tomatine |
| aucubin | emetine | magnosalin | tomentolide-a |
| axillarin | emodin | magnoshinin | tomentolide-b |
| Azulene | en-yn-dicycloether | mangiferin | tremulacin |
| baicalein | ent-16a-, 17-dihydroxy-kauran-19-oic-acid | mannitol | triethylcurcumin |
| baicalein-5,6,7-trihydroxy-flavone | ephedrine | margaspidin | trilobine |
| Baicalin | ephedroxane | marmin | tuberosine |
| baohuoside-1 | epicatechin | maslinic-acid | tylophorine |
| barbatoside-a | eriodictyol | matricine | umbelliferone |
| barbatoside-b | escin | matrine | ursolic-acid |
| bartsioside | esculetin | mauritianin | vanillic-acid |
| bassic-acid | esculin | menthol | verbascoside |
| bavachinin | eugenol | mesaconitine | vicenin-2 |
| bayachinine | eugenyl-acetate | methyl-7-kaempferol | vitamin-e |
| benzoxazinoids | euglobal | methyl-salicylate | vitexin |
| benzoylaconine | eupaformosanin | methysticin | wedelolactone |
| berbamine | eupahyssopin | Mufa | withaferin-a |
| berberastine | eupatolide | Mufas | withanolide |
| berberine | euxanthone | Myricetin | withanolide-d |
| bergapten | fagaramide | Myricitrin | wogonin |
| bergenin | faradiol | Myristicin | xanthotoxin |
| β-aescin | faradiol-monoester | n-hentriacontane | yangonin |
| β-amyrin | fenugreekine | naringenin | zingerone |
| β-amyrin-acetate | ferulic-acid | naringenin-7-o-beta-d-glucoside | zygophyllin |
| β-boswellic-acid | feruloyl-4-hydroxy-cinnamoyl-methane | Naringin | |
| β-damascenone | fetidine | neo-chlorogenic-acid | |
| β-escin | ficin | neoisoliquiritin | |

Other Agents

An additional antioxidant that may be used in the present invention is a phenylpropanoid glycosides. Martynoside, a particularly preferred phenylpropanoid glycoside, may be isolated from a number of botanical sources such as: *Clerodendron trichotomum* (apps1.niaid.nih.gov/struct_search/); the aerial section of *Scutellaria pontica*. (Ersoz T, et al., Turkish J. Chem. "Phenolic Compounds from *Scutellaria pontica*", which also provides the isolation of other phenylalkyloid glycosides); transformed root cultures of *Catalpa ovata* (Halina Wysokinska J, et al., *Free Radic Res.* 2003 August; 37(8):829-33); *Pedicularis plicata* (Liao R et al., *Phytotherapy Research* 1999 13(7):621-623; which also provides the isolation of verbascoside); *Pedicularis* (Wang et al., *Sci China C Life Sci* (1996) 39(2):154-8; which also provides the isolation of the phenylpropanoid glycosides: echinacoside, verbascoside, leucosceptoside A, and pediculariosides A, M and N). Their antioxidant scavenging activities are similar to those of the o-dihydroxy group of phenylpropanoid glycosides (Wang et al., *Biochem Pharmacol* (1996) 51(5): 687-91). The addition of martynoside or verbascoside as an ingredient in the formulation of the current invention is particularly advantageous because these phenylpropanoid glycosides have been shown to reduce fatigue in muscle tissue. This allows for a relaxation and smoothing in the overlying skin and reduces the signs of aging. (Liao R et al., *Phytotherapy Research* 1999 13(7):621-623).

Depigmenting agents may be added as an additional agent in the present invention. Depigmenting agents include tyrosinase inhibitors such hydroquinone and its derivatives (e.g., hydroquinone monomethyl ether, hydroquinone monoethyl ether, arbutin), soy and derivatives thereof, retinoids such as retinol; Kojic acid and its derivatives (e.g., kojic dipalmitate); transexamic acid; vitamins such as niacin, vitamin C and its derivatives; azelaic acid; phytic acid, licorice; mulberry extracts; extracts from *rumex* species such as *rumex crispus* extract; chamomile extracts; green tea extracts; lactic acid, pearl extract, Tricholoma matsutake extract, magnesiumasorbyl-phosphate, edelweiss extract, sedum acre extract, arbutine, ergothione, phyllantus emblica extract, α-MSH antagonists such as Undecylenoyl phenylalanine, germanium, and GABA and songyi mushroom. Bowman-Birk Inhibitors are described in U.S. Pat. No. 6,750,229 (e.g., inhibitors derived from the leguminosae, solanaceae, gramineae or cucurbitaceae family). Dermalight® and Clariskin3® from Silab are also depigmenting agents that can be used. Kinetin (N6 furfuryladenine) is a 6-(R-amino)purine cytokinin and is described in U.S. Pat. Nos. 5,602,139, 5,164, 394, and 5,021,422. It has been shown to have anti-aging effects on the skin of dogs as well as the depigmenting effects without adverse effects. (Kimura T, Doi K., *Rejuvenation Res.* 2004 Spring; 7(1):32-9).

Skin-protective lipids, such as ceramides, cerebrosides, essential fatty acids and botanical or marine oils containing these, calophyllum inophyllum squalene, squalane, botanical oils and butters such as (shea butter, meadowsweet oil and coconut oil) phospatidylserine, spingolipids and natural materials containing them such as Conyza Canadensis, phospholipids and sulfatet sterols available from Vincience may also be added to protect the skin.

Another particularly preferred skin-protective agent is beta glucan, which may be obtained from yeast, oat and mushroom species. It is a free radical scavenger and stimulates nonspecific immunity.

In some embodiments, an additional active ingredients included in the compositions of the present invention are compounds having sunscreening action. Sunscreening agents include, but are not limited to: aminobenzoic acid, avobenzone, dioxybenzone, homosalate, lisadimate, menthyl anthranilate, octocrylene, octyl methoxycinnamate, octyl salicylate, oxybenzone, padimate O, phenylbenzimidazole, roxadimate, sulisobenzone, titanium dioxide, trolamine salicylate, zinc oxide, hammamelitannin, and combinations thereof (see www.nlm.nih.gov/medlineplus/-druginfo/uspdi/202782.html). In one particular embodiment the sunscreen agent or agents are naturally occurring substances such as: zinc oxide, coffee oil, leuco-melanin, date palm fruit melanin, galanga extract (available from Symrise). Other substances that protect from UV damage that may be used include such as sanguinaria extract Krameria triandra root extract (15% neolignans) metallothionein, 1,25-dihydroxyvitamin D3, and thymidin dinucleotide. A preferred sun-protective extract is a polypodium leucomotos extract. This compound may be incorporated in the topical formulation, or alternatively, it may be provided as an oral supplement in addition to the formulation of the present invention for increased protection from UV damage. (Middlekamp-hup et al., *J Am Acad Dermatol,* 2004, 51(6) 910-918). One preferred sunscreen agent is isoamyl-p-methoxycinnamate (from Galanga, available from Symrise, Gmbh & Co); this compound provides an spf of greater than 30 using only natural ingredients (botanicals, antioxidants, coffe oil and microfine zinc oxide). Additional sunscreen agents include: allantoin, aloesin, apigenin, caffeic-acid, chlorogenic-acid, ellagic-acid, esculetin, esculin, ferulic-acid, fraxetin, fraxin, lawsone, p-aminobenzoic-acid, paba, procyanidins, rutin, silymarin, squalene, and umbelliferone.

Adding an anti-erythema ingredient to the formula, an additional effect caused by the damaging UV radiation besides free radical formation is addressed. The reduction in redness accomplished by applying the formulation of the present invention is due to an incorporation of aesculin, colchicines, esculin, glycyrrhetinic-acid, opc, opcs, procyanidin-a-2, procyanidins, rutin, or silymarin into the formulation.

Hyaluronic acid, a component of connective tissue whose function is to cushion and lubricate the tissue as well as hyaluronidase inhibitors such as extracts of *Echinacea* species are also useful as additional agents in the present formulation.

Alpha hydroxy acids, known for their exfoliating and resurfacing properties, may be combined as an ingredient in the topical formulation of the present invention in combination with a saccharide isomerate, green tea, strontium chloride and/or a COX 2 inhibitor to prevent stinging.

Hormonal decline is known to occur with aging therefore a class of substances replenishing and regulating these is useful in combination with the lipoic acid, carnosine, and carnitine formulation of the present invention. A non-exclusive list of agents useful for treating hormonal decline is: estriol, 7-ketodhea, dhea, estrone, estradiol, progesterone, pregnenolone, melatonin, soy isoflavons, phytoestrogens (back cohosh, red clover, sage etc.) chrysin, diosgenin, vitex extract, diindolmethane, pueraria mirifica (puresterol available from biobotanica), β-sitosterol, β-stigmasterol, betulin and derivatives thereof, *Conyza Canadensis* essential oil, and maca extract standardized to macamides.

Anti-acne agents may also be combined with the formulation of the present invention. Since both free radicals and inflammation are cofactors in acne, especially in adult skin, a combination with one or more anti-acne ingredient may be used in the topical formulation of the present invention. A non-limiting list of useful anit-acne agents includes: (−)-epigallocatechin, (−)-epigallocatechin-gallate, α-pinene, α-terpineol, anacardic-acid, azelaic-acid, baicalein, berberastine, berberine, β-carotene, camphor, caryophyllene, cryptotanshinone, δ-cadinene, γ-linolenic-acid, indole, linoleic-acid, nerolidol, pufa, pufas, pyridoxine, resorcinol, selenium, sulfur, terpinen-4-ol, thymol, tin, and zinc.

Agents having lipolytic activities for formulations targeting cellulite may also be combined with the formulation of the present invention. Metabolic decline especially regarding impaired lipid metabolism but also aging of skin due to AGES are factors in cellulite. Lipoic and carnosine and in particular carnitine in this invention target the deterioration of skin as presented in cellulite. Additional agents having lipolytic activities include, but are not limited to: 3-n-butyl-phthalide, adenosine, ajoene, alginates, allicin, alliin, amellin, bergapten, β-ecdysone, bromelain, chebulinic-acid, crocetin, cynarin, diallyl-disulfide, diallyl-sulfide, diallyl-trisulfide, dipropyl-disulfide, forskolin, ginsenoside-rb-2, imperatorin, inulin, nicotinic-acid, opc, opcs, oxypeucedanin, phellopterin, polydatin, resveratrol, s-allyl-cysteine-sulfoxide, s-methyl-1-cysteine-sulfoxide, saikosaponin, wogonin, and xanthotoxin.

Compounds having anticellulitic activities may be included as an additional ingredient in the formulation of the present invention. These compounds include, but are not limited to: aesculin, bromelain, esculin, theobromine, and theophylline. Additional anti-cellulitic compounds include caffeine, di-indolmethane, anti-estrogenic botanicals, *terminalia arjuna, garcinia cambodgia*, dihydromyricetin as found in Myriceline by Provital, as well as a citrus aurantium extract (see U.S. Pat. No. 6,224,873). This compound does not cross the blood/brain barrier and has minimal impact on α1,2 and β1,2 receptors and is therefore safer then caffeine, and/or ephedra containing agents. In one embodiment, no stimulants having a systemic effect if absorbed into the bloodstream is incorporated into the formulation.

Forskholin and other agents useful in raising cyclic AMP are also contemplated as ingredients in the present formulation.

Compounds having an anti-edemic activity are useful in combination with the formulation of the present invention. The prevention of swelling and fluid retention in the skin present in both face and body can be aided by combining an agent such as one of the following to the compound of the present invention. These compounds include, but are not limited to: (e)-4-(3',4'-dimethoxyphenyl)-but-3-en-ol, 10-acetoxy-8-hydroxy-9-isobutyloxy-6-methoxythymol, 13',ii8-biapigenin, 4-vinyl-guaiacol, 7-methoxycoumarin, acetyl-11-keto-β-boswellic-acid, actinidoles, aescin, α-amyrin, amentoflavone, anagyrine, anisodamine, anthocyanoside, arbutin, aristolochic-acid, aromaticin, artemetin, ascorbic-acid, asiaticoside, astringenin, aucubin, baicalein, baicalin, bavachinin, berberastine, berberine, β-aescin, β-amyrin, β-boswellic-acid, β-damascenone, β-escin, β-sitosterol, betulinic-acid, boehmerol-acetate, boldine, boswellic-acid, bradykininase, brazilin, bromelain, caffeic-acid, caryophyllene, caryophyllene-oxide, catechin, cis-spiroether, coniferyl-aldehyde, coumarin, crotaloburine, cryptolepine, curcumin, damascenine, digitoxin, diosmin, ephedrine, ephedroxane, escin, eugenol, eupahyssopin, faradiol, faradiol-monoester, friedelan-3-β-ol, gentianine, gentiopicroside, germacrone, ginkgetin, ginsenoside-r-o, glucose, glycyrrhetic-acid, glycyrrhetinic-acid, glycyrrhizin, gnaphaliin, hederagenin, helenalin, humulone, isoferulic-acid, kawain, lanceolarin, lapachol, lupeol, madecassoside, maslinic-acid, matricine, matrine, oleanolic-acid, opc, opcs, oxoushinsunine, paeonol, papain, papaverine, piperine, proanthocyanidins, procyanidin, procyanidins, pseudoephedrine, quercitrin, resveratrol, rosmarinic-acid, rutin, saikogenin, saikosaponin, sanguinarine, sciadopitysin, scopoletin, serrapeptase, sinapaldehyde, strophanthidin, syringaldehyde, taraxasterol, taraxasterol-acetate, taspine, tylophorine, umbelliferone, ursolic-acid, and withaferin-a.

Compounds having "anticapillary-fragility" activity may also be included as an additional ingredient. This causes telangiectasia and spider veins, which are preferably reduced are removed. Further, AGES and free radicals can cause damage to the fine vessels and induce telangiectasia or spider veins; therefore this class of agents is also useful. These agents include, but are not limited to: aescin, aesculetin, aesculetol, aesculin, aesculoside, diosmin, escin, esculetin, esculin, hederagenin, hesperidin, hydroxyethylrutoside, hyperoside, inulicin, luteolol, maniflavone, neoruscogenin, patulin, procyanidin-a-2, quercetol, quercetoside, rhamnetol, ruscogenin, rutin, rutoside, and xanthorhamnoside. Additionally, microcirculation decreases with age, especially around the eyes. Therefore this class is also beneficial and includes hydroxysuccinimide, chrysin(and other bilirubinolytic substances such as gardenin, gardenoside, berberine) or ingredients containing such substances eg Haloxyl from Sederma, Nattokinase, and vitamin K in all its forms including menaquinone-7.

Anti-elastase ingredients are also beneficial as' additional ingredients which enhance the formula's ability to firm the skin. These agents include, but are not limited to: PROTEA-SYL® TP LS 8657 (from Laboratories Serobiologique), anthocyanins, caffeic-acid, isoquercitrin, procyanidin-a-2, and quercetin. To help target sagging of skin, these ingredients can be included that improve adhesion of cells to the basement membrane and among themselves by enhancing synthesis of laminin V and integrin alpha 6. One such ingredient is Serilesine from Lipotec.

In a preferred embodiment, liposomes made by the process described by AGI Dermatics (New York) may be used. These photosomes and ultrasomes are be useful in formulations used to target DNA repair associated with photoaging and are described in U.S. Pat. Nos. 6,623,724 and 6,479,533. A marine-derived photolyase, a DNA-repair enzyme from Anacystis nidulans plankton may be added to the formulation. These enzymes, encorporated into a liposome (e.g., Photosome®) are adsorbed through the skin and repair sun-damaged DNA. Redness and sunburn cell formation may also be reduced or prevented by the addition of these enzymes.

Ethylenediaminetetraacetate (EDTA) or other metal chelators are preferred antioxidants that can be included in the compositions. Plant tannins are also metal chelators that may also be included in the composition. The chelating agent forms a complex with metal ions, inactivating them, and preventing them from affecting antioxidant activity. Other chelators include, but are not limited to dihydroxyethyl glycine, citric acid, tartaric acid, and mixtures thereof.

In one embodiment, acetyl-1 carnitine, carnosine, and lipoic acid or dihydrolipoic acid are formulated with the additional ingredients L-α glycerylphosphorylcholine, citicoline (a stabilized CDPCholine (cytidine 5'diphosphocholine) derivative) and huperzine-A. This formulation is particularly useful since the added ingredients enhance the effect of acetyl-1 carnitine and provide the skin with youthful amounts of acety-1 choline to prevent sagging and lack of tone to the face.

Of the additional agents described herein, 1, 2, 3, 4, 5, 6, 7, 8, 9, 10, or more additional agents may be added. The additional agents may be combined with the carnitine, carnosine, and lipoic acid formulation using any combination that one of ordinary skill in the art would perceive to combine. Two or more additional agents from one category (e.g., two AGE inhibitors) may be added to the same formulation. Since the combination of some of the additional agents may cause adverse effects not outweighed by their positive benefit when topically applied to the skin, care will be taken when making a topical formulation. Data from the FDA, research publications and any other known sources will be used to determine if there are known adverse interactions between any of the additional agents, lipoic acid, carnitine, and carnosine. Combinations with unacceptable adverse effects will not be used in the topical formulations of the present invention.

IV. Topical Formulations

The formulations of the present invention may also comprise derrmatologically acceptable topical auxiliaries. Dermatologically acceptable auxiliaries or carriers are those, which, as is known, can be used in the field of dermatology, pharmacology, food technology and related fields, in particular, those listed in relevant pharmacopeia (e.g. DAB Ph. Eur. BP NF), and other auxiliaries whose properties do not impede physiological use when applied to the skin.

Suitable carriers may be lubricants, wetting agents, emulsifying and suspending agents, preservatives, antiirritants, emulsion stabilizers, film formers, gel formers, odor masking agents, resins, hydrocolloids, solvents, solubilizers, neutralizing agents, permeation accelerators, pigments, quaternary ammonium compounds, refatting and superfatting agents, ointment, cream or oil base materials, silicone derivatives, stabilizers, sterilizing agents, propellants, drying agents, opacifiers, thickeners, waxes, emollients, or white oils.

According to the invention, the formulations are administered transdermally (topically). The topical administration provides the lipoic acid, carnosine, and carnitine composition directly to the skin, and is preferably provided with the use of a dermatologically acceptable carrier. While the carrier may consist of a relatively simple solvent or dispersant, such as an oil, it is generally preferred that the carrier comprise a material more conducive to topical application, and particularly one, which will form a film or layer on the skin to which it is applied. This localizes the application and provides some resistance to perspiration and/or aids in percutaneous delivery and penetration of the active ingredients into lipid layers. Many such compositions are known in the art, and can take the form of creams, gels, ointments, hydrogels, pastes or plasters, and liquid dosage forms, such as solutions, emulsions, in particular oil-in-water emulsions, suspensions, for example lotions etc, or even solid sticks. Liposomes or microspheres may also be used.

Preferably, the lipoic acid, camosine, and carnitine are soluble per se in the carrier, or they are effectively solubilized (e.g. as an emulsion or microemulsion). It is necessary that the carrier be inert in the sense of not bringing about a deactivation of the active ingredients, reducing the stabilization effects of the active ingredients, and not causing any adverse effect on the skin areas to which it is applied.

Suitable carriers include water, alcohols, oils and the like, chosen for their ability to dissolve or disperse the active ingredients at concentrations of active ingredients most suitable for use in the therapeutic treatment. Generally, even low concentrations of active ingredients in the carrier will be suitable, requiring only the more frequent application of the topical composition. One particular embodiment comprises the use of novel dispersions of hydrophobes to yield a surfactant-free formulations, by subjecting the materials to high pressure, high shear processing. Cold process formulations are also a preffered method as they protect certain heat-sensitive agents in the formulation, they can be obtained by using self-emulsifying oleosomes such as Natrulon OSF available from Lonza.

In one embodiment, the formulation is processed using the carriers and dry-water process of Aerosil® (Degussa), which is based on fumed silica. (see www1.sivento.com/wps3/portal/en/aerosil/industries/persona10.html).

The formulation may be administered as part of a makeup such as a facial powder, foundation, rouge, or eye shadow. In these formulations, a colorant is preferably added.

It is contemplated that in addition to the lipoic acid, carnosine, and camitine topical formulation, a capsule or other oral dosage form containing one or more antioxidants may be taken in addition to the topical administration of the formulation (which alternatively contains one or more antioxidants as well.) This allows for an increased protection for the skin.

Only effective amounts of each of a lipoic acid, a carnosine, and a carnitine are needed to treat the signs of aging in skin. Generally, an effective amount of the topical formulation is applied to exposed or affected skin sites in association with a carrier, and particularly one in which the active ingredients are soluble per se or are effectively solubilized (e.g. as an emulsion or microemulsion).

By the term "an effective amount" of a compound or property, e.g., an amount effective in reducing or eliminating the effects of AGE as provided herein, is meant such amount as is capable of performing the function of the compound or property for which an effective amount is expressed. As pointed out above, the exact amount required will vary from case to case, depending on recognized variables such as the compounds employed and the individual subject treated. Thus, it is not possible to specify an exact "effective amount." However, an appropriate effective amount may be determined by one of ordinary skill in the art using only routine experimentation.

Preferably, the formulation will contain 0.001 to 50% by weight lipoic acid. Desirably, it will contain 0.1%-7.0% by weight, or more preferably 0.5-1.5% by weight lipoic acid. Preferably, the formulation will contain 0.01 to 50% carnitine, desirably 0.025%-5% by weight, or even more preferably 0.5%-2% by weight carnitine. Preferably, the formulation will contain 0.01 to 50% by weight carnosine. desirably, it will contain 0.1%-7.0% by weight, or more preferably 0.5-1.5% by weight carnosine. Carriers can be chosen which will solubilize or disperse the active ingredients at such concentrations as provided herein. Some particularly efficacious embodiments contain 1-5% by weight of an R-lipoic acid, 1-5% by weight acetyl-L-carnosine, and 1-5% by weight acetyl-L-carnitine in a liposomal carrier.

Encapsulation

In one aspect of the present invention, the composition is stabilized using microencapsulation. Microencapsulation can protect the active agents from the surrounding environment and increase the effectiveness as an anti-aging agent. Processes conventionally used for microencapsulation may be employed, and may comprise encapsulation by nanosomes, liposomes, or other vehicles known in the art.

Microencapsulation is particularly useful for compositions containing DHLA. It is available in liquid form and is thereby more prone to degradation and oxidation than R-lipoic acid. Therefore, encapsulation of the DHLA will protect and extend the activity of the formulation.

The microcapsules may be prepared, for example, by coacervation techniques or by interfacial polymerization, for example, hydroxymethylcellulose or gelatin-microcapsules and poly(methylmethacrylate) microcapsules, respectively, in colloidal drug delivery systems (for example, liposomes, albumin microspheres, microemulsions, nano-particles and nanocapsules) or in macroemulsions. (Remington's Pharmaceutical Sciences (A. Osol ed., 16th ed. (1980)).

One typical process is to dissolve the shell material in a solvent (in the form of a colloidal or true solution) and to disperse the core material in the resulting solution in the form of solids or microdroplets. This dispersion is divided into microdroplets and then heated using, for example, hot air. During this process, the solvent evaporates and the shell material reprecipitates in the form of solids and forms a shell around the core material. This gives crude microcapsules, which can then be subjected to the customary processing steps and incorporated into the final formulations. This process utilizes the known phenomenon of coacervation.

Another method of microencapsulation uses interface polymerization to create the microcapsule shell. In this method, precursors of the shell material, for example monomers, are concentrated onto the core material, where they polymerize to give the final shell film. Fat-coating processes also may be used.

The materials used for microencapsulation are selected from conventional hydrophilic or hydrophobic substances or mixtures thereof. Solids, in particular natural polymers, for example, starch and other polysaccharides, are preferred. However, synthetic polymers can also be used. Examples of shell materials are fats and/or waxes, preferably those having a solidification temperature of approximately 35°-80° C. and include mixtures of cetyl palmitate and cetyl alcohol. Other compounds include: polysaccharides and their derivatives of natural or partially synthetic origin, (e.g. cellulose derivatives); furthermore polymers of $\alpha$- and/or $\beta$-hydroxycarboxylic acids, in particular polymers of glycolic acid (polyglycolides), lactic acid (polylactides), $\alpha$.-hydroxybutyric acid (polyhydroxybutyrate), $\alpha$-hydroxyvaleric acid (polyhydroxyvalerate) and/or their copolymers, or mixtures of such polymers and/or copolymers.

Independently of the specific technique for preparing the microcapsules, it is preferred to carry out the process at a temperature which does not cause any of the components of the formulation to decompose or lose their antioxidant activity.

Similarly, nanoencapsulation may be used. Nanoemulsions are metastable oil-in-water emulsions having a globule size is less than 150 nm. They can be stabilized with amphiphilic lipids Nanoemulsions are structurally distinct from microemulsions which are thermodynamically stable dispersions comprising micelles of at least one amphiphilic lipid swollen with oil and do not require mechanical energy to be prepared. An advantage of using nanoencapsulation is the reduced need for surfactants, which may tend to lead to intolerance and entailing a sticky feel when applied to the skin. (see U.S. Pat. No. 6,562,356).

In one embodiment, the formulation is encapsulated in cyclodextrine such process is performed for instance by the Wacker group.

In another embodiment the the formulation is encapsulated with NADH, R-DHLA, ATP, Glutathione and SOD in Nano Spheres. Such process is performed for instance by Salvona Technologies. In another embodiment biopolymer nanoemulsions from Ivrea-Pak Tech are used to eliminate undesirebale residue ("ghosting") commonly associated with porous particulate entrapment formulations.

To prepare the dermatological compositions according to the invention, the active ingredients can be mixed or diluted with a suitable auxiliary (excipient). Excipients can be solid, semisolid, or liquid material, which may serve as vehicle or carrier medium for the active ingredient. The other auxiliaries, if desired, are mixed in the manner known to the person skilled in the art. One particular agent marketed as Cosmoperine, an extract from black pepper (from Sabinsa Co, N.J.), may be used to enhance penetration of the ingredients through the skin.

If desired, two or more active ingredient components can be formulated together. For example, R-lipoic acid and R-dihydrolipoic acid may be combined in the formulation, or L-carnosine may be combined with a copper anserine.

Generally, the composition is topically applied to the affected skin areas in a predetermined or as-needed regimen to bring about improvement, it generally being the case that gradual improvement can occur with each successive application. The application may occur over a short term (i.e., one application, or application for one week) or over a long term (i.e., the formulation may be applied daily for a month, a year, etc.).

Methods of Increasing ATP Formation

In addition or as an alternative to adding additional ingredients such as additional mitochondrial antioxidants, in a preferred aspect of the present invention, ATP formation in the skin can be encouraged by the application of a microcurrent or LED light. Using microcurrent or light in addition to the topical formulation of the present invention provides for enhanced penetration of the active agents into the skin as well as increased production of ATP.

The formulation described herein may be administered using a micro-current. The micro-current is administered at the same or within several minutes of time when the topical formulation is applied to the skin. The current used is preferably from 1-300 mA. The use of a micro-current will enhance the effects of the topical formula in preventing mitochondrial decline as current in this range is known to enhance ATP formation. Additionally, LED light, such as blue and red LED lights can be used or without the current simultaneously with the above topical preparation to enhance the collagen formation in the skin.

In one embodiment, the device for administering the microcurrent has four electrodes for emitting microcurrent. The conductive materials of the electrodes are selected so it will not produce allergic reactions on the skin, and are preferably made from titanium, stainless steel, carbon, gold, platinum, silver, glass, or fiberglass coated with a transparent conductive material such as mineral oxides, cotton swabs, sponges, or sponge-like materials. The electrodes are preferably immersed in water or a solution containing the water soluble topical formulations described in this invention. Titanium is a preferred electrode material because of its ability to remain unaffected when in contact with the skin, and because it does not cause irritating reactions when in contact with sensitive skin. The electrodes may be, for example, rigid comb or probe-like pads of various shapes, or comprised of flexible bristles having the same or similar conductive properties. In one embodiment, the electrodes are pencil-shaped with spherical tips comprising sponge-like attachments designed to ergonomically fit the shape of the subjects face, cheekbone, chin, undereye-area or other areas on the body where the current is intended to be applied in a targeted manner.

Therefore, in one embodiment of the current invention, the microcurrent is applied by (a) providing a plurality of electrodes connected to an electrical source defining at least four channels to provide a microcurrent of electricity across the facial tissue or other area of skin; (b) positioning the pair of electrodes on the patient; (c) providing a controlled current from about 10 µA to about 250 µA in each channel at a frequency of up to 500 Hz; and (d) providing a first frequency to at least one channel and a second frequency to at least one other channel to provide an interferential waveform.

The electrodes can be in contact with the topical formulation in the form of a cream, gel or liquid, which is directly applied to the skin. Alternatively, the electrodes can be in direct contact with the skin and the topical formulation applied to electrode-skin contact points. The topical formulation is applied onto the skin immediately before or during application of the current. In one embodiment, the topical formulation is directed in the form of a spray onto the skin at or near the electrodes. In another particular embodiment, this sprayed formulation is delivered via an oxygen concentrator that provides the additional benefit of oxygenating the skin ATP synthesis is maximized in the Krebs cycle in the presence of oxygen.

The microcurrent can be delivered as a localized stimulation (i.e., to the eye area) rather than broad area stimulation by the use of multiple (i.e., 2, 3, 4, 5, or 6) contact points and two or more frequencies arranged in a circular, square or other closed figure pattern. In order to obtain the maximum anti-aging skin treatment effect, it is generally desirable to apply the skin treatment device to precise locations. The present invention is especially well adapted to provide precisely focused microcurrent to the face and surrounding areas of the eyes, acupuncture points, or facial muscles.

In one embodiment, it is desirable to move the electrodes providing the microcurrent over the skin about the location where skin treatment is desired. The microcurrent can be varied in frequency, waveform and voltage in order to target various skin levels and subcutaneous muscles. In one embodiment, the microcurrent is administered through a ZnO-coated glass tip.

In a particular embodiment, the current is applied in a targeted way to the attachments or the belly of particular facial and body muscles that contribute to the saggy appearance associated with aging. A particular technique is used to tone these particular muscles via the Golgi-tendon response. One such technique is described in U.S. Pat. No. 4,957,480, herein incorporated by reference, which teaches that a different effect can be achieved by, for example, firmly pressing the electrode onto the skin or moving it over the skin, changing the placement of the electrodes relative to the muscles, or changing the amperage, frequency, polarity, or duration of the current. The muscles can be relaxed, toned, strengthened, compressed or energized dependant upon the method used, and provide superior improvement to the appearance of skin. For instance, to relax the muscles in the face or neck, moistened electrode tips are pressed firmly against the skin of the face in overlying relation to the middle of a muscle, and then the moistened tips are respectively and simultaneously moved toward the opposite ends of the muscle or toward the insertion and origin of a muscle. This movement results in a relaxation and thus lengthening of the muscles. The actual length of the muscle being treated may be such that its origin lies beyond the face as into the hairline, whereas the insertion or movable end of that muscle will generally be inserted in the face. A galvanic current adjusted to produce a current of about 300 to about 640 microamperes is used at a high frequency of about 30 to about 99 hertz, and alternating in polarity from positive to negative polarity for duration of about 1 to about 4 seconds.

Particular pads may be used with the microcurrent administration of the topical formulation of the present invention. In some embodiments, the topical formulation will be administered using a device or method designed to more readily break the skin barrier and provide the agents in the topical formulation with a faster or more effective means through the stratum corneum. These include, for example, oxygen nebulizers and nanosomal mist in conjunction with iontophoresis. A spray or nebulizer may be used to create the nanosomel mist. In one embodiment, the micro-electronic cosmetic delivery mechanism described as PowerCosmetics™ may be used for delivery of the topical agent to the skin. This method is useful for delivering ionizable compounds to the skin and aids the penetration of small molecules through the stratum corneum. (www.powerpaper.com). This can be described as an electronic patch.

Light can be used as an energy source to encourage ATP formation and also enhance the penetration of active agent into the skin. The light may be intense pulse light (IPL) or any other non-invasive LED or soft laser illumination. In one embodiment, the light stimulation used in combination with a topical mitochondrial antioxidant applied concurrently with a microcurrent.

Neck and face areas are more sensitive, in general, to light stimulation compared to the rest of the body and, therefore, their treatment requires less power. Therefore, in one embodiment, the preferred wavelength ranges and powers, as described in U.S. Pat. No. 6,063,108 for chronic inflammation in tissue other than the face, is 800-1,100 nm at 20-100 mW. For inflammation of the face, preferred wavelength ranges and powers are 800-960 nm at 30-100 mW.

The light source is preferably a LED or an array of LEDs. The light from the LED may be, for example, red light at 625 nm or 660 nm, magenta light at 850, infra red light at 940 nm, blue light at 420 nm, or amber light at 590 nm. Alternatively, a combination of these and other LEDs may be used. In one embodiment, blue LEDs and red LEDs are combined.

U.S. Pat. Pubs. 20030009158 and 20040049247, herein incorporated by reference, demonstrate the use of light having a wavelength of 400-500 nm to treat aging skin. The methods disclosed may be used in addition to the microcurrent and topical application disclosed herein.

When light is added to the method of the present invention, it is particularly preferred in one embodiment to provide a compound in the topical formulation that enhances light penetration of the stratum corneum such as α-hydroxy acids (e.g., glycolic acid) to the topical formulation. See U.S. Pat. Pubs. 2003 0009158 and 2004 0049247, which use light having a wavelength of 400-500 nm to treat aging skin.

As used herein, the term "treatment of aging skin" means the treatment of the symptoms of skin damage due to either chronoaging or photoaging of the skin, which is characterized by wrinkles, loss of elasticity, and hyper-pigmentation. The treatment is effective to enhance the appearance and/or health of the skin. This includes, for example, increasing the amount of collagen in the skin, reducing oxidative damage, and preventing or reducing the amount of AGE in the skin.

As used herein, the term "reducing mitochondrial decay" means decreasing the ATP production and/or increasing the mitochondrial free radicals that destroy different vital parts of the mitochondria. The mitochondrial decay is reduced by at least 20%, or more preferably at least 30%, or more preferably at least 40%, or even more preferably at least 50%. In one embodiment, the mitochondrial decay is reduced by at least 60% or at least 70%.

The reduction in mitochondrial decay is measured using a skin biopsy. The skin biopsy may be obtained, cultured, and quantitated by any method known in the art. In particular, a skin biopsy obtained from a biopsy site at which the topical formulation was applied is taken and cultured. The levels of ATP are then measured. The fibroblasts can be cultured and measured as described in Greco M, et al., (FASEB J. 10.1096/fj.02-1009fje. Published online Jul. 18, 2003 or in Levtchenko E N et al., Pediatric Research 59:287-292 (2006)).

Following long-standing patent law convention, the terms "a" and "an" mean "one or more" when used in this specification. Each patent described herein is hereby incorporated by reference in its entirety.

EXAMPLES OF TOPICAL COSMETIC

Preparations of the Invention

The following Examples are provided to illustrate the invention without being limiting in any way.

EXAMPLE 1

| Active Ingredient | % by weight |
|---|---|
| R-lipoic acid | 5.0 |
| acetyl-l-carnitine | 2.0 |
| carnosine | 1.0 |
| astaxanthin | 1.0 |
| tocotrienol | 0.50 |
| tocopherol | 0.50 |
| sesame oil | 1.0 |
| grape proanthocyanidin | 0.50 |
| E.D.T.A. (ethylenediamine tetracetic acid) | 0.05 |

EXAMPLE 2

| Ingredient | % by weight |
|---|---|
| R-lipoic acid | 1.0 |
| acetyl-l-carnitine | 1.0 |
| carnosine | 1.0 |
| benfotiamine | 0.2 |
| bilberry anthocyanins | 1.0 |
| rosmarinic acid | 0.5 |
| shark derived glycosaminoglycans | 1.0 |
| tocopherols | 0.5 |

EXAMPLE 3

| Ingredient | % by weight |
|---|---|
| R-dihydrolipoic acid | 1.0 |
| acetyl-l-carnitine | 2.0 |
| carnosine | 1.0 |
| lutein | 0.5 |
| tetrahexyldecylascorbate | 3.0 |
| lycopene | 0.5 |
| coenzyme Q10 (ubiquinone) | 0.1 |
| curcumine | 0.5 |

EXAMPLE 4

| Ingredient | % by weight |
|---|---|
| R-lipoic acid | 1.0 |
| R-dihydrolipoic acid | 1.0 |
| acetyl-l-carnitine | 1.0 |
| carnosine | 3.0 |
| NADH | 1.0 |

EXAMPLE 5

| Ingredient | % by weight |
|---|---|
| R-lipoic acid | 1.0 |
| acetyl-l-carnitine | 1.0 |
| carnosine | 3.0 |
| Pyruvate | 1.0 |

EXAMPLE 6

| Ingredient | % by weight |
|---|---|
| R-dihydrolipoic acid | 1.0 |
| acetyl-l-carnitine | 1.0 |
| carnosine | 3.0 |
| dipalmitoyl-hydroxy-proline | 1.0 |
| wolfberry extract | 1.0 |

EXAMPLE 7

| Ingredient | % by weight |
|---|---|
| R-lipoic acid | 2.0 |
| l-carnitine | 2.0 |
| l-carnosine | 2.0 |
| l-glutathione | 1.0 |
| Bilberry anthocyanins | 2.0 |
| Rosemary extract | 1.0 |
| Myristicin | 1.0 |

EXAMPLE 8

| Ingredient | % by weight |
|---|---|
| R-lipoic acid | 1.0 |
| l-carnitine | 2.0 |
| l-carnosine | 2.0 |
| Huperzine-A | 0.5 |
| polyenylphosphatidylcholine | 1.0 |

Having described the invention with reference to particular compositions, theories of effectiveness, and the like, it will be apparent to those skilled in the art that it is not intended that the invention be limited by such illustrative embodiments or mechanisms, and that the modifications can be made without departing from the scope or spirit of the invention, as defined by the appended claims. It is intended that all modifications and variations be included with the scope of the invention. The claims are meant to cover the claimed components and steps in any sequence that is effective to meet the objectives there intended, unless the context specifically indicates the contrary.

What is claimed is:

1. A method of treating skin, said method comprising administering a topical composition comprising:
   (a) 5.0% R-lipoic acid,
   2.0% acetyl-1-carnitine,
   1.0% carnosine,
   1.0% astaxanthin,
   0.5% tocotrienol,
   0.5% tocopherol,
   1.0% sesame oil,
   0.5% grape proanthocyanidin, and
   0.05% E.D.T.A. (ethylenediamine tetracetic acid);
   (b) 1.0% R-lipoic acid,
   1.0% acetyl-1-carnitine,
   1.0% carnosine, 0.2% Benfotiamine,
1.0% bilberry anthocyanin,
0.5% rosmarinic acid,
1.0% shark derived glycosaminoglycan, and
0.5% tocopherol;
(c) 1.0% R-dihydrolipoic acid,
2.0% acetyl-1-carnitine,
1.0% carnosine,
0.5% lutein,
3.0% tetrahexyldecylascorbate,
0.5% lycopene,
0.1% coenzyme Q10 (ubiquinone), and
0.5% curcumine;
(d) 1.0% R-lipoic acid,
1.0% R-dihydrolipoic acid,
1.0% acetyl-1-carnitine,
3.0% carnosine, and
1.0% NADH;
(e) 1.0% R-dihydrolipoic acid,
1.0% acetyl-1-carnitine,
3.0% carnosine,
1.0% dipalmitoyl-hydroxy-proline, and
1.0% wolfberry extract;
(f) 2.0% R-lipoic acid,
2.0% 1-carnitine,
2.0% 1-carnosine,
1.0% 1-glutathione,
2.0% bilberry anthocyanin,
1.0% rosemary extract, and
1.0% myristicin;
or
(g) 1.0% R-lipoic acid,
2.0% 1-carnitine,
2.0% 1-carnosine,
0.5% Huperzine-A, and
1.0% polyenylphosphatidylcholine;
and a dermatologically acceptable carrier;
wherein amounts are in weight percent and said composition is effective in the treatment of skin.

2. The method of claim 1, wherein the composition comprises:
5.0% R-lipoic acid,
2.0% acetyl-1-carnitine,
1.0% carnosine,
1.0% astaxanthin,
0.5% tocotrienol,
0.5% tocopherol,
1.0% sesame oil,
0.5% grape proanthocyanidin, and
0.05% E.D.T.A. (ethylenediamine tetracetic acid);
and a dermatologically acceptable carrier.

3. The method of claim 1, wherein the composition comprises:
1.0% R-lipoic acid,
1.0% acetyl-1-carnitine,
1.0% carnosine,
0.2% benfotiamine,
1.0% bilberry anthocyanin,
0.5% rosmarinic acid,
1.0% shark derived glycosaminoglycan, and
0.5% tocopherol;
and a dermatologically acceptable carrier.

4. The method of claim 1, wherein the composition comprises:
1.0% R-dihydrolipoic acid,
2.0% acetyl-1-carnitine,
1.0% carnosine,
0.5% lutein,
3.0% tetrahexyldecylascorbate,
0.5% lycopene,
0.1% coenzyme Q10 (ubiquinone), and
0.5% curcumine;
and a dermatologically acceptable carrier.

5. The method of claim 1, wherein the composition comprises:
1.0% R-lipoic acid,
1.0% R-dihydrolipoic acid,
1.0% acetyl-1-carnitine,
3.0% carnosine, and
1.0% NADH;
and a dermatologically acceptable carrier.

6. The method of claim 1, wherein the composition comprises:
1.0% R-dihydrolipoic acid,
1.0% acetyl-1-carnitine,
3.0% carnosine,
1.0% dipalmitoyl-hydroxy-proline, and
1.0% wolfberry extract;
and a dermatologically acceptable carrier.

7. The method of claim 1, wherein the composition comprises:
2.0% R-lipoic acid,
2.0% 1-carnitine,
2.0% 1-carnosine,
1.0% 1-glutathione,
2.0% bilberry anthocyanin,
1.0% rosemary extract, and
1.0% myristicin;
and a dermatologically acceptable carrier.

8. The method of claim 1, wherein the composition comprises:
1.0% R-lipoic acid,
2.0% 1-carnitine,
2.0% 1-carnosine,
0.5% Huperzine-A, and
1.0% polyenylphosphatidylcholine;
and a dermatologically acceptable carrier.

9. The method of claim 1, wherein the carnosine is L-carnosine.

10. The method of claim 1, wherein the topical composition further comprises nicotinamide-adenine-dinucleotide.

11. The method of claim 1, wherein the topical composition further comprises an antioxidant.

12. The method of claim 1, wherein the topical composition further comprises an AGE inhibitor.

13. The method of claim 1, wherein the topical composition further comprises a mitochondrial resuscitant.

14. The method of claim 13, wherein the mitochondrial resuscitant is NTBHA, Mn-SOD, COQ10, creatine, D-ribose, pyruvate or stabilized ATP.

15. The method of claim 14 wherein the mitochondrial resuscitant is NTBHA.

16. The method of claim 1, wherein the topical composition further comprises a collagen enhancing agent, a sunscreen agent, an anti-edemic agent, a glutathione or an inducers thereof, a collagenase-inhibitor, an anti-inflammatory agent, a phenylpropanoid glycoside, a depigmenting agent or agent addressing hyperpigmentation, a skin-protective lipids, hyaluronic acid, an alpha hydroxy acid, an agent useful for treating hormonal decline, an anti-acne agent, an agent altering lipolytic activity, an anti-cellulitic agent, an agent altering anti-capillary-fragility, an anti-elastase agent, an anti-erythema agent, or an agent that raises cyclic AMP.

17. The method of claim 1, wherein the composition is encapsulated.

18. The method of claim 17, wherein the composition is encapsulated in a liposome.

19. The method of claim 1, wherein the composition is administered in a makeup.

20. The method of claim 19, wherein the makeup is a foundation, a cover cream, or an eyeshadow.

21. The method of claim 1, further comprising applying electricity to the skin.

22. The method of claim 21, wherein the electricity is applied using an electronic patch or a portanble electronic device.

23. The method of claim 1, further comprising applying light to the skin.

24. The method of claim 21, further comprising applying light to the skin.

* * * * *